US012805952B2

(12) United States Patent
McDiarmid et al.

(10) Patent No.: US 12,805,952 B2
(45) Date of Patent: Nov. 24, 2026

(54) ROBOTIC SURGICAL SYSTEM WITH CONTROL DRIVE ASSEMBLY FOR SINGLE PORT SURGICAL TECHNIQUES

(71) Applicant: COVIDIEN LP, Mansfield, NC (US)

(72) Inventors: Ian McDiarmid, West Sussex (GB); Brian King, Stowmarket (GB); Jon Cooke, Cambridge (GB); Aki Hannu Einari Laakso, Raleigh, NC (US); Hans Christian Pflaumer, Apex, NC (US); Akshaya Ahuja, St. Neots (GB); Chace F. Medeiros, Raleigh, NC (US); Rupert Anthony Barton, Cheltenham (GB); Thomas Henry Brittain, Bury St Edmunds (GB); James Angus Boonzaier, Cape Town (ZA); Austin Paul Davis, Wendell, NC (US); Robert Ian Noakes, Cambridgeshire (GB); Matthew Michael Marinovich, London (GB); Andre Fraser Monteiro, Cambridgeshire (GB); Marcus Joseph Wolf, Cambridge (GB); Jozsef Horvath, Wake Forest, NC (US); Adrian Edward Cooper, Cambridgeshire (GB); Paul Smitheman, Cambridge (GB); Mark J. Pawulski, Saffron Walden (GB); Brian Gregory Holmes, Raleigh, NC (US)

(73) Assignee: Covidien LP, Mansfield, MA (US)

( * ) Notice: Subject to any disclaimer, the term of this patent is extended or adjusted under 35 U.S.C. 154(b) by 157 days.

(21) Appl. No.: 18/836,490

(22) PCT Filed: Mar. 10, 2023

(86) PCT No.: PCT/US2023/015027

§ 371 (c)(1),
(2) Date: Aug. 7, 2024

(87) PCT Pub. No.: WO2023/172759

PCT Pub. Date: Sep. 14, 2023

(65) Prior Publication Data

US 2025/0114155 A1 Apr. 10, 2025

Related U.S. Application Data

(60) Provisional application No. 63/341,459, filed on May 13, 2022, provisional application No. 63/269,158, filed on Mar. 10, 2022.

(51) Int. Cl.
*A61B 34/30* (2016.01)
*A61B 1/00* (2006.01)
(Continued)

(52) U.S. Cl.
CPC .......... *A61B 34/30* (2016.02); *A61B 1/00149* (2013.01); *A61B 1/0016* (2013.01);
(Continued)

(58) Field of Classification Search
CPC .............. A61B 1/00149; A61B 1/0016; A61B 2034/302; A61B 34/30; A61B 50/13; A61M 25/0113
See application file for complete search history.

(56) References Cited

U.S. PATENT DOCUMENTS

2016/0184034 A1 6/2016 Holop et al.
2021/0015572 A1* 1/2021 Gomez .................. A61B 34/35
2021/0290314 A1 9/2021 Sachs et al.

FOREIGN PATENT DOCUMENTS

CN 106510849 A 3/2017
CN 111227939 A 6/2020
(Continued)

OTHER PUBLICATIONS

International Search Report and Written Opinion dated Aug. 10, 2023 for International Application No. PCT/2023/015027 (18 pages).
(Continued)

*Primary Examiner* — Scott Luan
(74) *Attorney, Agent, or Firm* — Carter, DeLuca & Farrell LLP

(57) ABSTRACT

A robotic surgical system includes an instrument cart having a setup arm assembly and a control drive assembly coupled to the setup arm assembly. The control drive assembly includes a chassis assembly, a first drive unit and a second drive unit mounted to the chassis assembly, and a leadscrew assembly. Each drive unit is positioned to translate relative
(Continued)

to the chassis assembly between a retracted position and an advanced position. The first drive unit couples to a first surgical instrument and the second drive unit couples to a second surgical instrument. The leadscrew assembly is mounted to the chassis assembly and includes a first leadscrew operably associated with the first drive unit and a second leadscrew operably associated with the second drive unit. The first leadscrew rotates to cause the first drive unit to translate relative to the chassis assembly. The second leadscrew rotates to cause the second drive unit to translate relative to the chassis assembly.

15 Claims, 25 Drawing Sheets

(51) Int. Cl.
*A61B 50/13* (2016.01)
*A61M 25/01* (2006.01)

(52) U.S. Cl.
CPC ........ *A61B 50/13* (2016.02); *A61B 2034/302* (2016.02); *A61M 25/0113* (2013.01)

(56) References Cited

FOREIGN PATENT DOCUMENTS

| | | |
|---|---|---|
| WO | 2018041211 A1 | 3/2018 |
| WO | 2021161162 A1 | 8/2021 |

OTHER PUBLICATIONS

Anonymous, "Stepper Motor Driven 11" Leadscrew—Sherline Products", Dec. 2020 available at: https://web.archive.org/web/20201201002317/https://www.sherline.com/product/6590 6591-stepper-motor-driven-11-leadscrew.

* cited by examiner

ROBOTIC SURGICAL SYSTEM WITH CONTROL DRIVE ASSEMBLY FOR SINGLE PORT SURGICAL TECHNIQUES

CROSS-REFERENCE TO RELATED APPLICATIONS

The present application is a U.S. National Stage Application filed under 35 U.S.C. § 371(a) of International Application Serial No. PCT/US2023/015027 filed on Mar. 10, 2023 which claims the benefit of and priority to U.S. Provisional Patent Application Ser. No. 63/269,158, filed on Mar. 10, 2022, and U.S. Provisional Patent Application Ser. No. 63/341,459, filed on May 13, 2022, the contents of which are being incorporated herein in their entirety.

TECHNICAL FIELD

This disclosure relates to robotic surgical systems and, more particularly, to a control drive assembly for a single port robotic surgical system.

BACKGROUND

Robotic surgical systems include control drive assemblies supporting surgical instruments used in laparoscopic and/or robotic surgery. These surgical instruments generally have a proximally located actuating mechanism that is operably coupled to a control drive unit of the control drive assembly for actuating distal end effectors of the surgical instruments. The control drive unit includes any number of motors operably associated with the actuating mechanisms of the surgical instruments. A clinician remotely controls these motors to enable the surgical instruments to robotically perform a surgical task within a body cavity of a patient, and often in remote locations within the body cavity that are not easily accessed without robotic surgical systems.

SUMMARY

According to an aspect of this disclosure, a robotic surgical system includes an instrument cart having a setup arm assembly, and a control drive assembly coupled to the setup arm assembly. The control drive assembly includes a chassis assembly, a first drive unit and a second drive unit mounted to the chassis assembly, and a leadscrew assembly mounted to the chassis assembly. Each drive unit of the first and second drive units is positioned to translate relative to the chassis assembly between a retracted position and an advanced position. The first drive unit is configured to couple to a first surgical instrument, the second drive unit is configured to couple to a second surgical instrument. The leadscrew assembly includes a first leadscrew operably associated with the first drive unit and a second leadscrew operably associated with the second drive unit, the first leadscrew being rotatable to cause the first drive unit to translate relative to the chassis assembly, the second leadscrew being rotatable to cause the second drive unit to translate relative to the chassis assembly.

In aspects, the chassis assembly may include a spinebox assembly that supports the leadscrew assembly therein. The first and second drive units may be movably mounted to the spinebox assembly. The first leadscrew may support a first slide plate assembly that engages with the first drive unit and the second leadscrew may support a second slide plate assembly that engages with the second drive unit. The first and second slide plate assemblies may be movable through the spinebox assembly to move the first and second drive units relative to the spinebox assembly. The first slide plate assembly may include drive pins extending therefrom. The drive pins may be positionable within the first drive unit to couple the first slide plate assembly to the first drive unit. The first slide plate may be threadedly coupled to the first leadscrew. The first slide plate may be positioned to translate along the first leadscrew as the first leadscrew is rotated relative to the first slide plate.

In aspects, the first drive unit may include a first motor assembly supporting a first plurality of motors configured to operate the first surgical instrument. The second drive unit may include a second motor assembly supporting a second plurality of motors configured to operate the second surgical instrument.

In aspects, the leadscrew assembly may further include a drive assembly supported on the chassis assembly. The drive assembly may include one or more leadscrew drivetrain motors that mount to the chassis assembly. The leadscrew drive train motors may be operatively coupled to one or more drive gears. The drive gears may be rotatable by the leadscrew drivetrain motors to rotate the first and/or second leadscrews.

In aspects, a manual release assembly may include one or more release knobs. The release knobs are operatively coupled to one or more drive gears to manually rotate the first and/or the second leadscrews.

In aspects, a robotic surgical system includes a setup arm assembly and a control drive assembly pivotably coupled to the setup arm assembly. The control drive assembly includes an endoscope, a surgical instrument, and a control drive unit. The control drive unit includes a chassis assembly, an endoscope drive unit mounted to the chassis assembly and removably supporting the endoscope, an instrument drive unit mounted to the chassis assembly and removably supporting the surgical instrument, a first leadscrew operably associated with the endoscope drive unit, and a second leadscrew operably associated with the instrument drive unit. The first leadscrew is rotatable to cause the endoscope drive unit to translate relative to the chassis assembly. The second leadscrew is rotatable to cause the instrument drive unit to translate relative to the endoscope drive unit.

In aspects, the surgical instrument may define an instrument centerline and the second leadscrew may define a leadscrew centerline. The instrument centerline and the leadscrew centerline may be offset.

In aspects, the control drive unit may include a support bar assembly, wherein movement of the support bar may cause the control drive unit to pivot relative to the setup arm assembly. The support bar assembly may include a first portion and a second portion that are selectively attachable to one another about the chassis assembly by a joint. The first portion of the support bar assembly may be arched distally to a port latch assembly. The port latch assembly may include a fixed clamp arm and a pivotable clamp arm. The pivotable clamp arm is positioned to pivot relative to the fixed clamp arm to secure a surgical portal assembly to the support bar assembly. The surgical portal assembly may define a first lumen therethrough configured to receive the endoscope and a second lumen therethrough configured to receive the surgical instrument therethrough. The surgical portal assembly may have a proximal housing that defines a first annular channel configured to receive the fixed clamp arm therein and a second annular channel configured to receive the pivotable clamp arm therein. The first and/or second lumens may include a lofted distal portion to enable greater shaft deflections of the endoscope or the surgical instrument at the distal end portion of the surgical portal assembly in comparison to a proximal portion of the surgical portal assembly.

In aspects, the setup arm assembly may include a control pad that is actuatable to cause the endoscope drive unit and/or the instrument drive unit to move relative to the chassis assembly. The setup arm assembly may include one or more brake assemblies configured to limit movement of the endoscope drive unit and the instrument drive unit relative to the chassis assembly.

In aspects, the instrument drive unit may include a first sterile adapter assembly secured thereto and the endoscope drive unit may include a second sterile adapter assembly secured thereto. Each of the first and second sterile adapter assemblies supports drive dogs therein. The endoscope drive unit and/or the instrument drive unit includes a drive dog alignment tool that pre-aligns the drive dogs of the respective first or second sterile adapter assemblies for facilitating attachment of the respective endoscope or surgical instrument to the respective first or second sterile adapter assemblies.

According to one aspect, this disclosure is directed to a control drive assembly for a robotic surgical system. The control drive assembly includes a chassis assembly, an endoscope drive unit, a first instrument drive unit, a second instrument drive unit, a third instrument drive unit, and a manual release assembly. The chassis assembly supports a leadscrew assembly, the leadscrew assembly including a plurality of leadscrews. The endoscope drive unit is coupled to an endoscope, the first instrument drive unit is coupled to a first surgical instrument, the second instrument drive unit is coupled to a second surgical instrument, and the third instrument drive unit is coupled to a third surgical instrument. The endoscope drive unit and each instrument drive unit are mounted to the chassis assembly, wherein each drive unit is movable relative to the other drive units to move the endoscope, the first surgical instrument, the second surgical instrument, or the third surgical instrument between extended and retracted positions relative to the chassis assembly in response to rotation of one or more leadscrews of the plurality of leadscrews. The manual release assembly includes one or more release knob operatively coupled to the leadscrew assembly. The one or more release knobs are rotatable to manually rotate one or more of the plurality of leadscrews.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate aspects of this disclosure and, together with a general description of this disclosure given above, and the detailed description given below, explain the principles of this disclosure, wherein.

DETAILED DESCRIPTION

Figure 1:
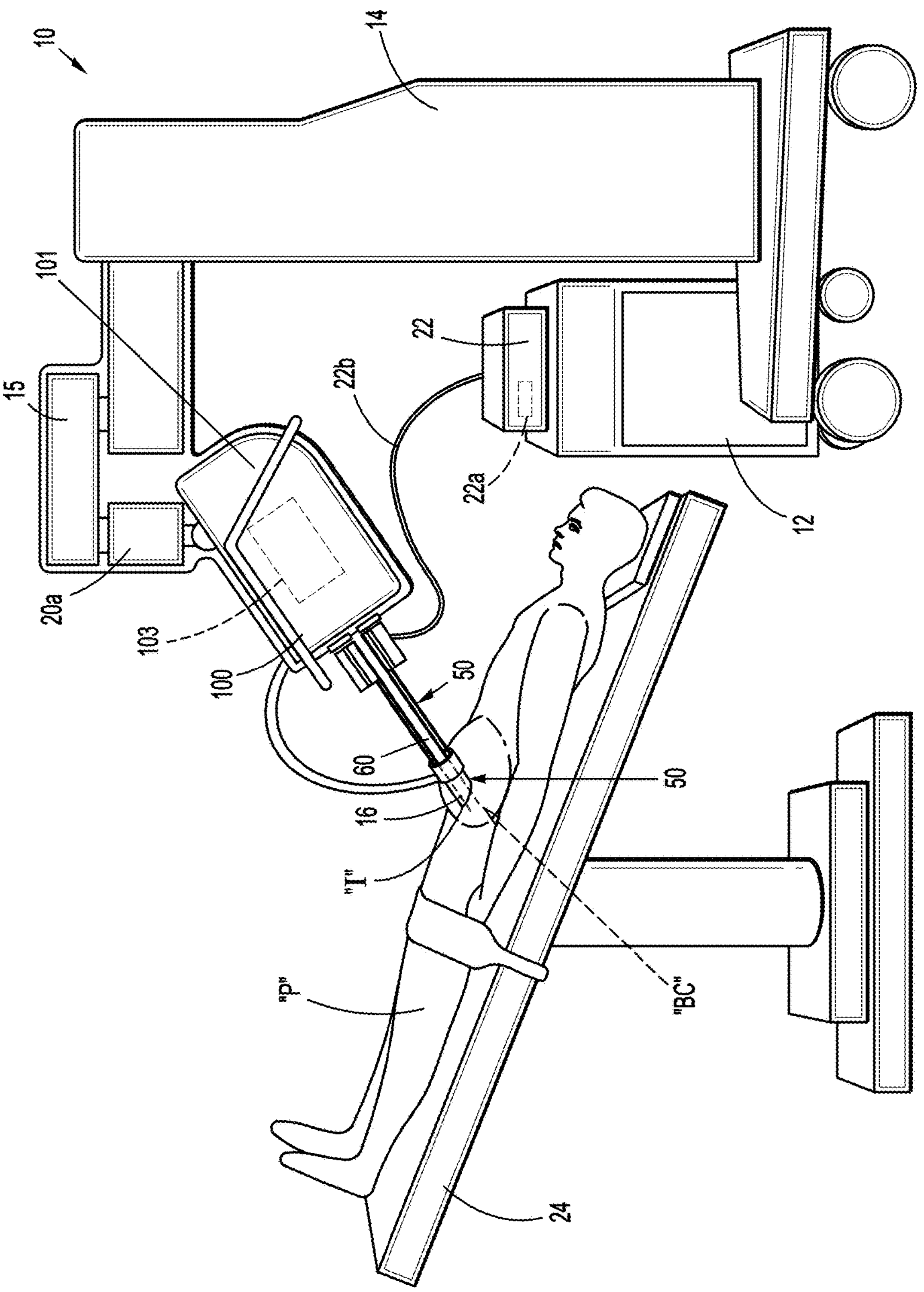
FIG. 1 is a perspective view of a robotic surgical system being used for a surgical procedure on a patient in accordance with the principles of this disclosure.
Figures 1A, 1B:
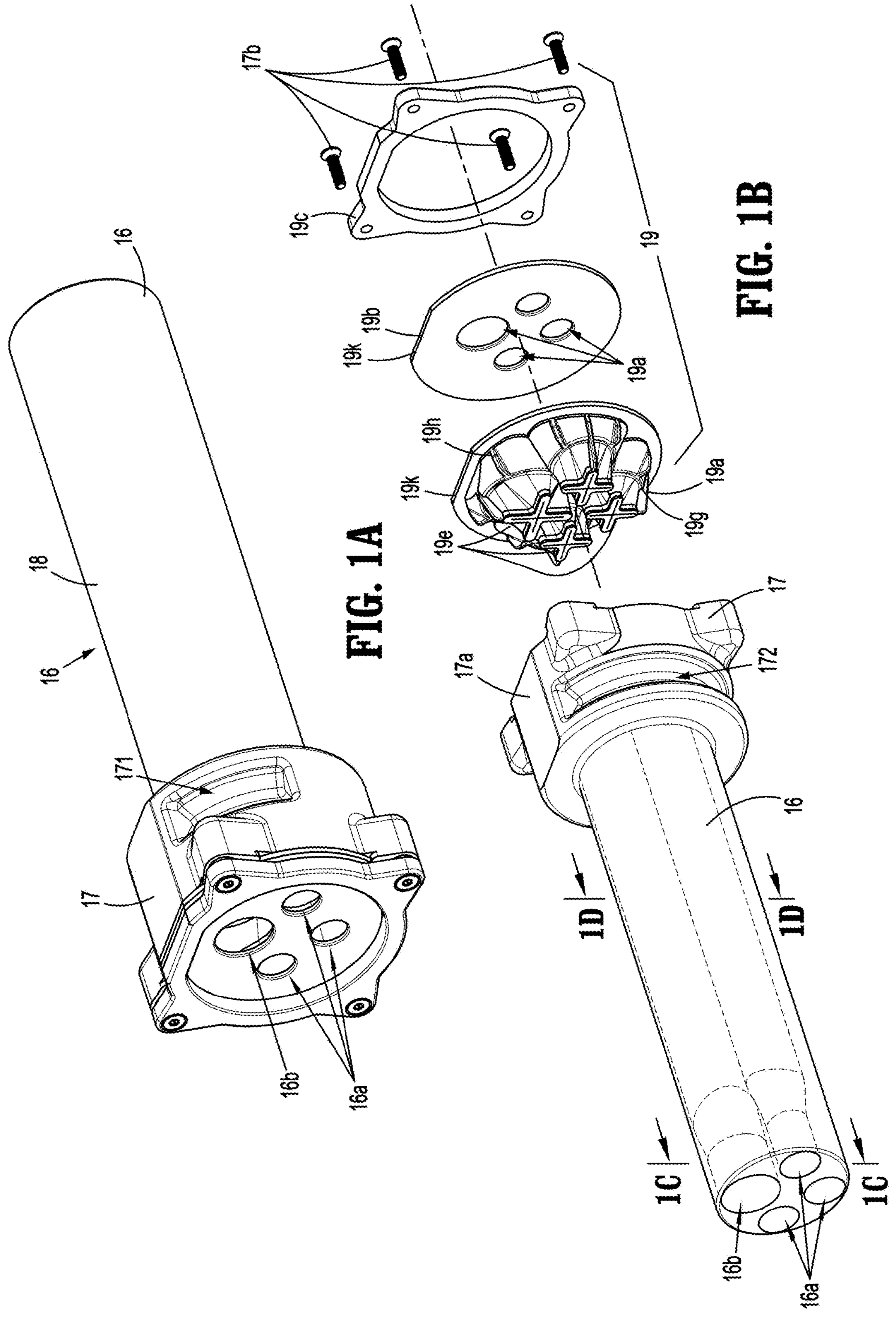
FIG. 1A is an enlarged, perspective view of a surgical portal assembly of the robotic surgical system of FIG. 1.
FIG. 1B is a perspective view, with parts separated, of the surgical portal assembly of FIG. 1A.

Aspects of this disclosure are described in detail with reference to the drawings, in which like reference numerals designate identical or corresponding elements in each of the several views. As used herein, the term "distal" refers to that portion of structure closer to a patient, while the term "proximal" refers to that portion of structure, farther from the patient. As used herein, the term "clinician" refers to a doctor, nurse, or other care provider and may include support personnel and/or equipment operators.

In the following description, well-known functions or constructions are not described in detail to avoid obscuring the present disclosure in unnecessary detail.

Robotic surgical systems have been used in minimally invasive medical procedures. Such procedures may be referred to as what is commonly referred to as "Telesurgery." These robotic surgical systems have one or more surgical instruments removably coupled thereto. Such surgical instruments include, for example, endoscopes, electrosurgical forceps, cutting instruments, staplers, graspers, electrocautery devices, or any other endoscopic or open surgical devices. Prior to or during use of the robotic surgical system, various surgical instruments can be selected and connected to the robotic surgical system for selectively operating end effectors of the connected surgical instruments.

Figure 2A:
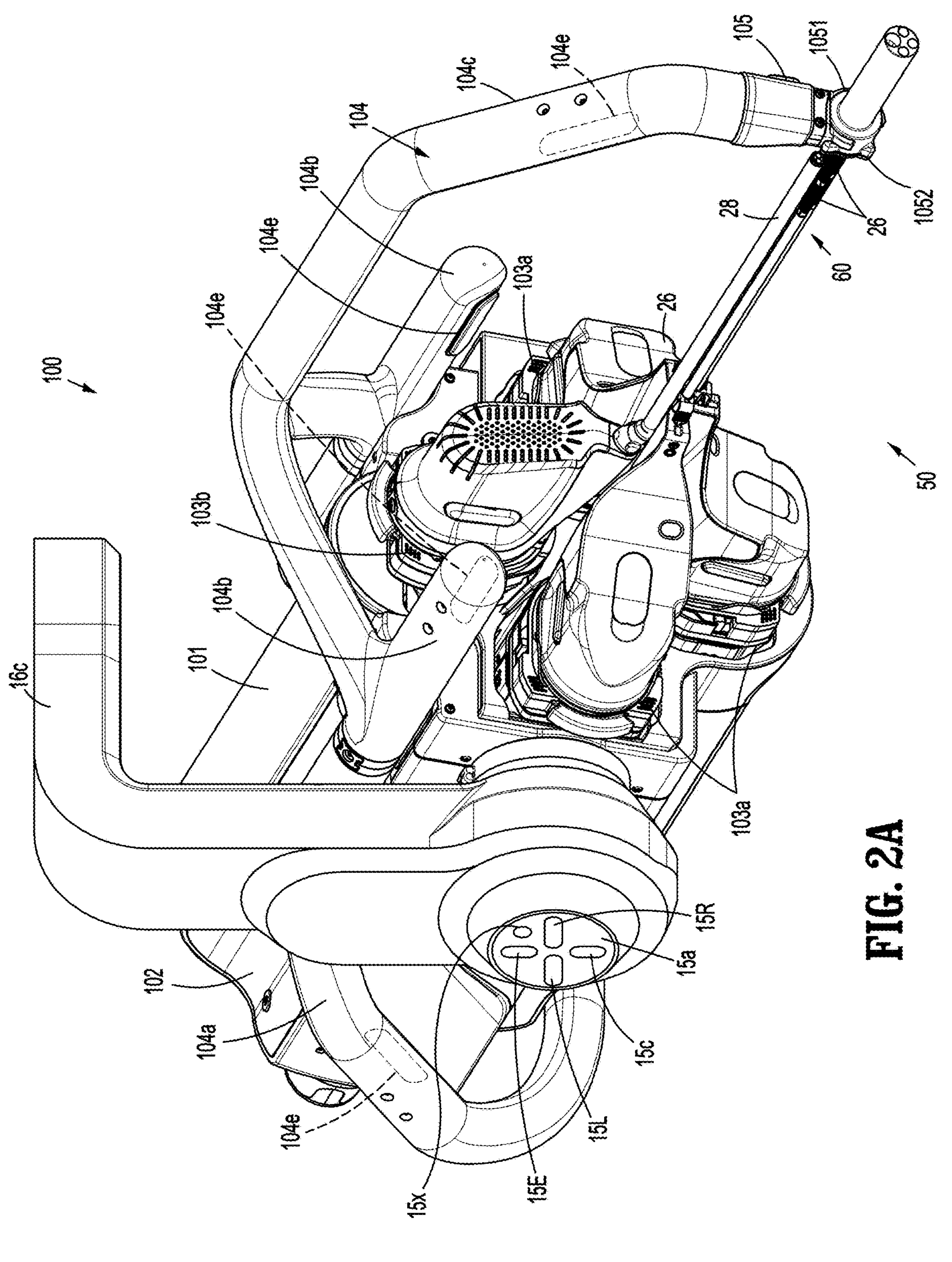
FIG. 2A is an enlarged, front, perspective view of a control drive assembly of the robotic surgical system of FIG. 1.
Figure 2B:
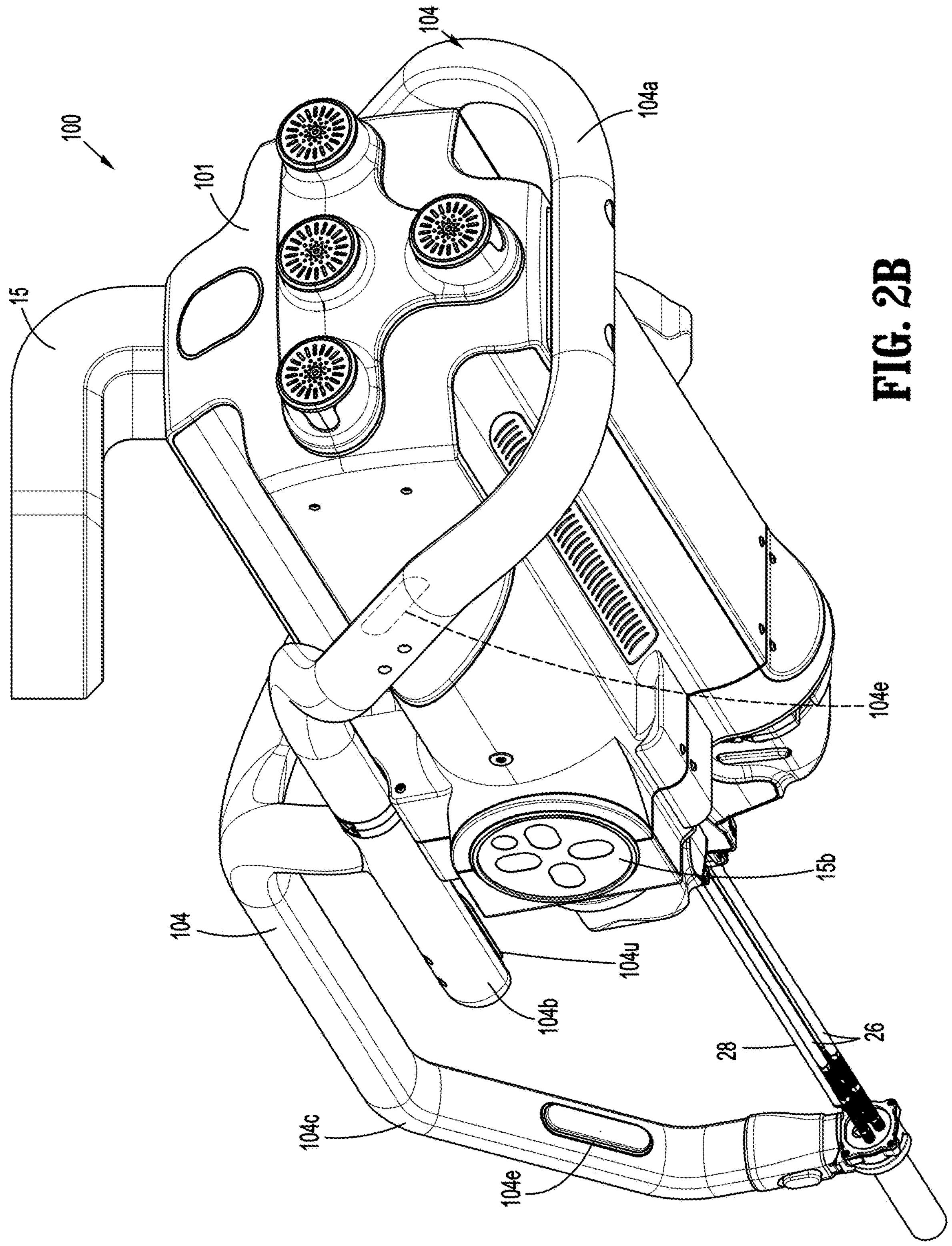
FIG. 2B is an enlarged, rear, perspective view of the control drive assembly of FIG. 2A.
Figure 3:
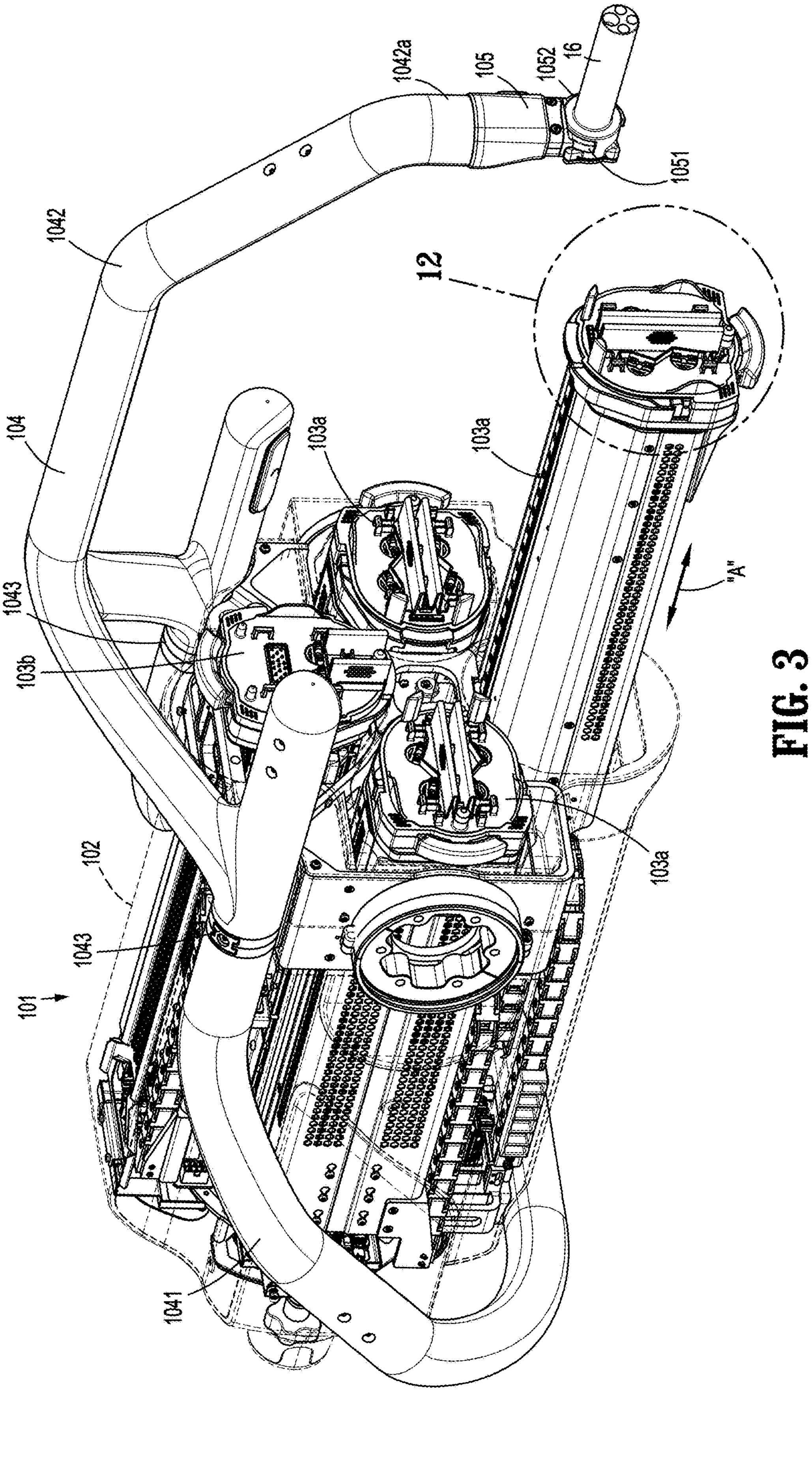
FIG. 3 is a front, perspective view of a control drive unit of the control drive assembly of FIGS. 2A and 2B, the control drive unit shown with portions thereof shown in phantom for clarity.
Figure 4:
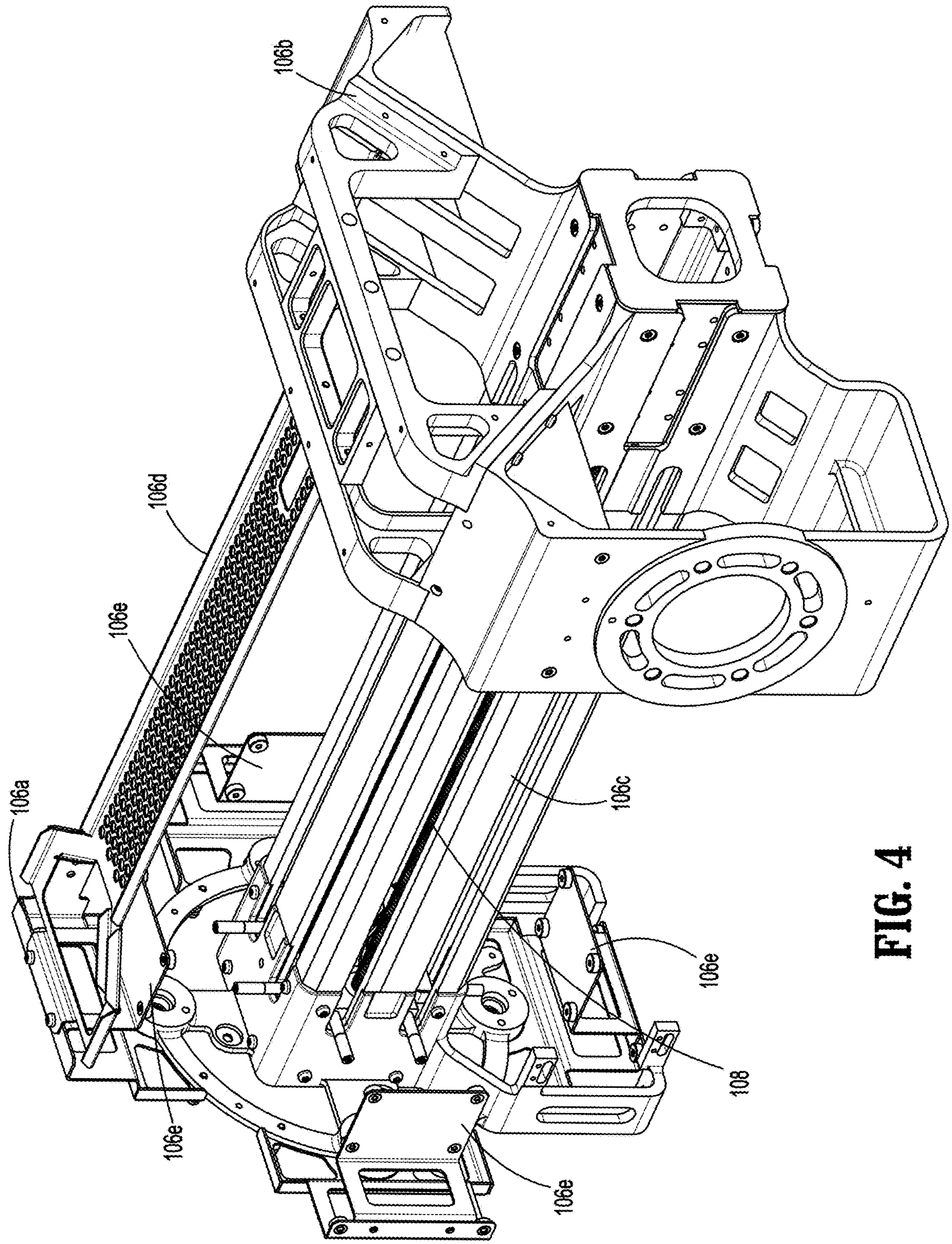
FIG. 4 is a front, perspective view of a chassis assembly and a leadscrew assembly of the control drive unit of FIG. 3.
Figure 5:
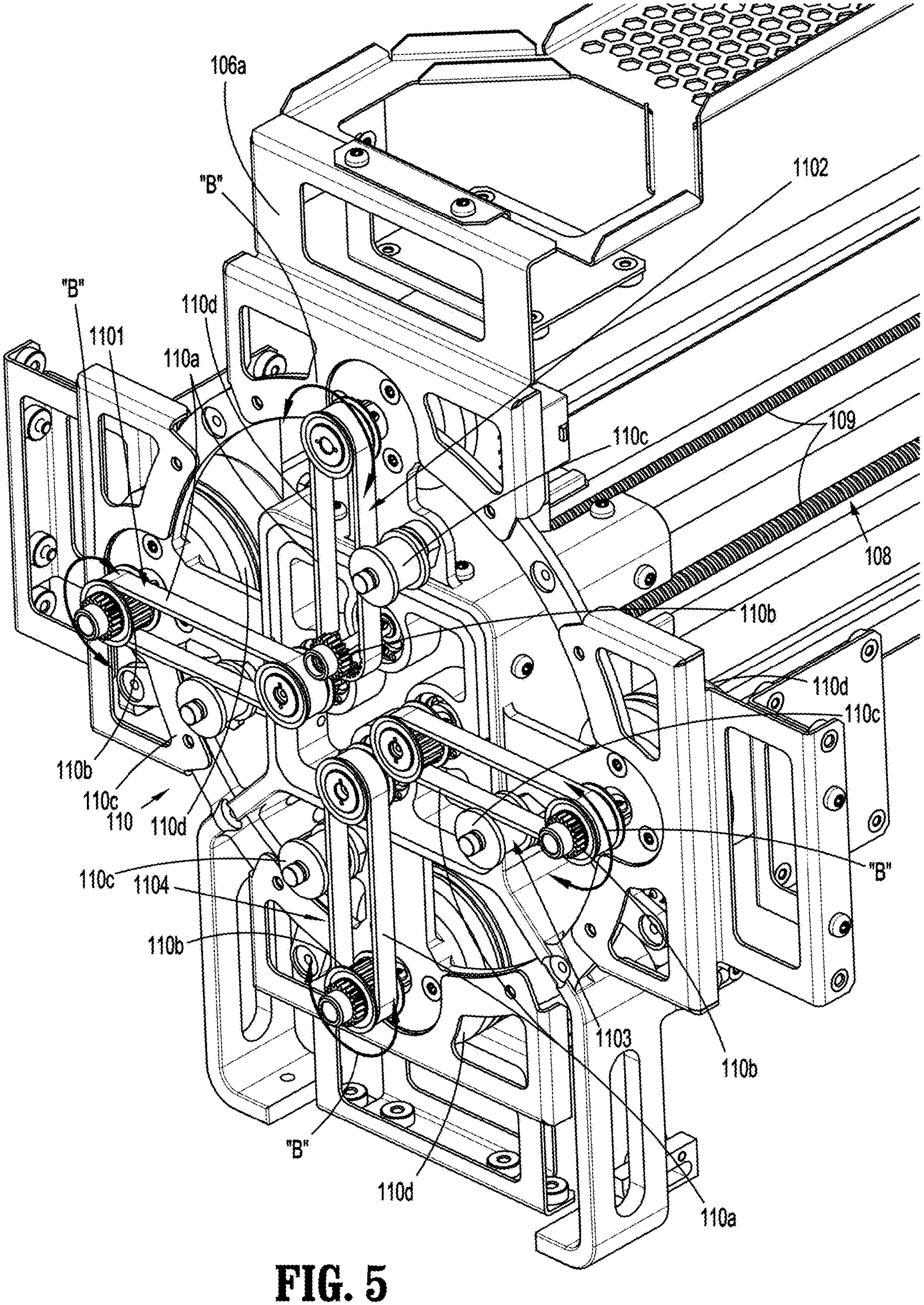
FIG. 5 is an enlarged, rear, perspective view of a proximal portion of FIG. 4 with leadscrew drivetrain motors shown attached thereto.
Figure 7:
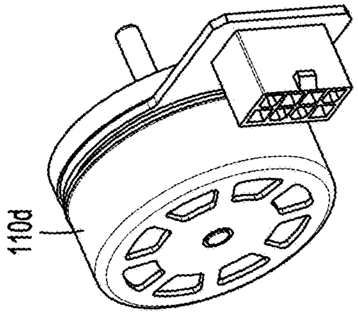
FIG. 7 is an enlarged, front, perspective view of one of the leadscrew drive train motors shown in FIG. 6.
Figure 6:
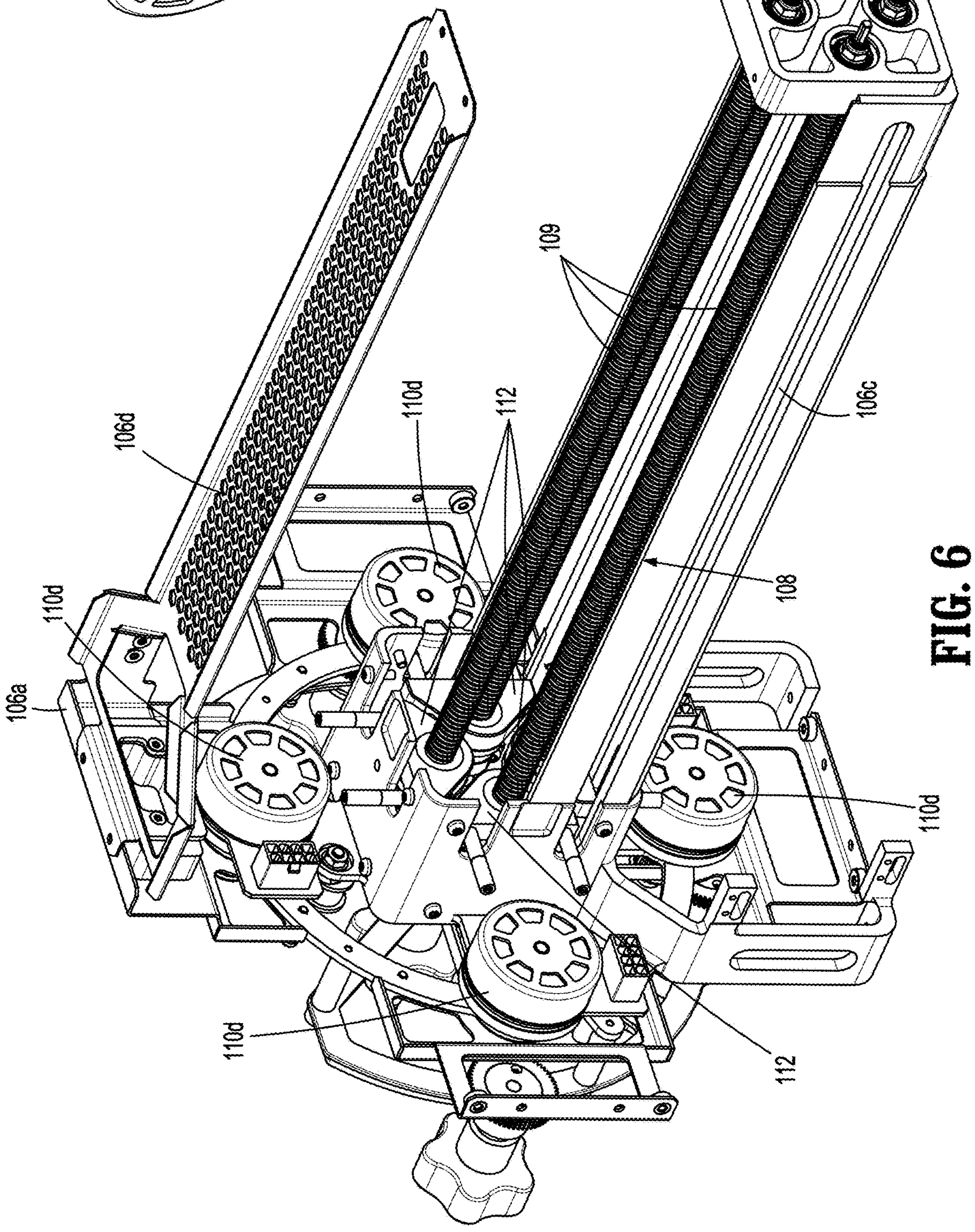
FIG. 6 is an enlarged, front, perspective view of FIG. 4 with portions of the chassis assembly removed for clarity, and with a manual release assembly and the leadscrew drivetrain motors of FIG. 5 shown attached thereto, and with slide plate assemblies of the leadscrew assembly shown in retracted positions.

With reference to FIGS. 1, 2A, 2B, a robotic surgical system is shown generally at 10. Robotic surgical system 10 employs various robotic elements to assist the clinician and allow remote operation (or partial remote operation) of surgical instruments 60 of surgical instrument systems 50 of robotic surgical system 10. Various controllers, circuitry, robotic arms, gears, cams, pulleys, electric and mechanical motors, etc. may be employed for this purpose and may be designed with surgical system 10 to assist the clinician during an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

Robotic surgical system 10 includes a workstation 12 and an instrument cart 14. The instrument cart 14 supports a control drive assembly 100 on a setup arm assembly 16 that is selectively movable relative to instrument cart 14. Control drive assembly 100 includes one or more surgical instrument systems 50 mounted on a control drive unit 101 supported on setup arm assembly 15. Control drive unit 101 is movable relative to cart 14 and houses an instrument drive assembly 103 for manipulating the surgical instrument systems 50 and/or independent surgical instruments 60 thereof with the assistance of, for example one or more computing devices or controllers. Instrument drive assembly 103 can include an instrument drive unit 103*a* for operating surgical devices such as graspers coupled thereto and an endoscope drive unit 103*b* for operating surgical devices such as an endoscope coupled thereto. Surgical instrument system 50 can include any number and/or type of surgical instruments. The surgical instruments 60 can include, for example, graspers or forceps 26, which may be electrosurgical, an endoscope 28, and/or any other suitable instrument that can be driven by one or more associated tool drives, such as instrument drive unit 103*a* and endoscope drive unit 103*b* of instrument drive assembly 103. For example, besides graspers 26 and endoscope 28, the one or more surgical instruments 60 can include dexterous tools, such as grippers, needle drivers, staplers, dissectors, cutters, hooks, graspers, scissors, coagulators, irrigators, suction devices, which are used for performing a surgical procedure.

With reference to FIGS. 1 and 1A-1E, surgical instrument system 50 further includes a surgical portal assembly 16 defining a plurality of separate and spaced-apart conduits, channels or lumens 16*a*, 16*b* therethrough that are configured to receive, for instance, the surgical instruments 60 for accessing a body cavity "BC" of a patient "P." Such lumens 16*a*, 16 may be of any suitable shape and/or size. In other aspects, the surgical portal assembly 16 may define a single conduit, channel, or lumen therethrough that is configured to receive, for instance, the surgical instruments 60 for accessing a body cavity "BC" of a patient "P." In particular, the surgical portal assembly 16 can be inserted through an incision "I" and into the body cavity "BC" of the patient "P". Surgical portal assembly 16 includes a proximal housing assembly 17 and an elongated shaft 18 extending distally from proximal housing assembly 17. Proximal housing assembly 17 supports a seal assembly 19 that includes a cross-slot valve assembly 19*a*, a diaphragm 19*b* supported on the cross-slot valve assembly 19*a*, and a clamp assembly 19*c* that secures diaphragm 19*b* and cross-slot valve assembly 19*a* to a proximal housing 17*a* of proximal housing assembly 17 via fasteners 17*b*. Proximal housing assembly 17 further defines a first annular channel 171 and a second annular channel 172 in an outer side surface of proximal housing 17*a*. First and second annular channels 171, 172 are separate and distinct and disposed on opposed sides of proximal housing 17*a*. Diaphragm 19*b* defines a plurality of openings 19*d* therethrough that align with lumens 16*a*, 16*b* and cross-slot valves 19*e* of cross-slot valve assembly 19*a*. Openings 19*d* function to maintain insufflation pressure when an instrument is advanced therethrough. Cross-slot valves 19*e* are biased in a closed position (FIG. 1B), but are openable when an instrument is passed therethrough. Cross-slot valves 19*e* function as seals configured to facilitate sealed insertion of surgical instruments through tissue "T" of the patient "P" and to help maintain the body cavity "BC" in an insufflated state when such instruments are not present. Cross-slot valves 19*e* further include reinforcement ribs 19*g*, 19*h* to prevent valve prolapse in response to instrument removal. Clamp assembly 19*c* is rigid and defines a central aperture 19*f* therethrough for providing access to elongated shaft 18 through diaphragm 19*b* and cross-slot valve assembly 19*a*. Diaphragm 19*b* and cross-slot valve assembly 19*a* each include a keyed edge 19*k*(e.g., flat edge) that interrupts the rounded circumference thereof to facilitate proper alignment of diaphragm 19*b* and cross-slot valve assembly 19*a* with lumens 16*a*, 16*b*, since such lumens may have different sizes relative to one another.

Figure 1C:
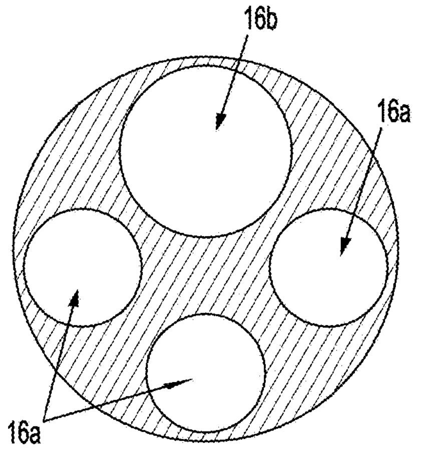
FIG. 1C is a cross-sectional view of the surgical portal assembly of FIG. 1B as taken along section line 1C-1C shown in FIG. 1B.
Figure 1D:
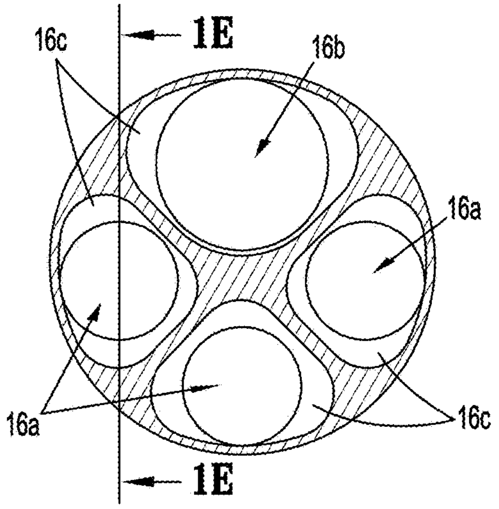
FIG. 1D is a cross-sectional view of the surgical portal assembly of FIG. 1B as taken along section line 1D-1D shown in FIG. 1B.
Figure 1E:
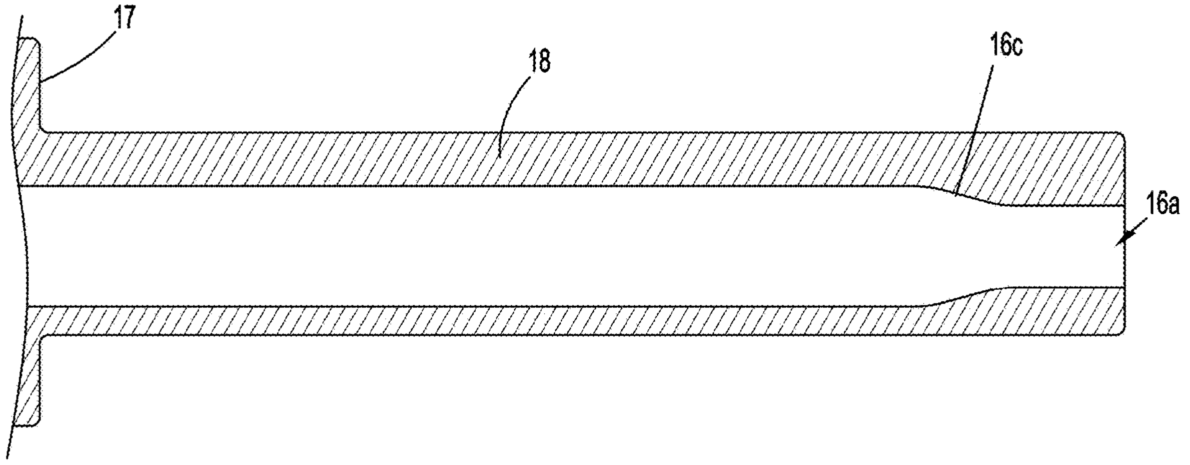
FIG. 1E is a cross-sectional view of the surgical portal assembly of FIG. 1B as taken along section line 1E-1E shown in FIG. 1D.

Briefly, as illustrated in FIGS. 1C-IE, lumens 16*a*, 16*b* have tapered or lofted portions 16*c*, for example, at distal end portions thereof, to enable increased instrument shaft deflections as the surgical instruments are advanced therethrough.

With reference again to FIG. 1, the workstation 12 includes an input device 22 in communication with control drive unit 101 for use by a clinician to control the surgical portal assembly 16 and the various surgical instrument systems 50 (and surgical instruments 60 thereof) via the instrument drive assembly 103 for performing surgical operations on the patient "P" while the patient "P" is supported on a surgical table 24, for example. Input device 22 is configured to receive input from the clinician and produces input signals. Input device 22 may also be configured to generate feedback to the clinician. The feedback can be visual, auditory, haptic, or the like.

The workstation 12 can further include computing devices and/or controllers such as a master processor circuit 22*a* in communication with the input device 22 for receiving the input signals and generating control signals for controlling the robotic surgical system 10, which can be transmitted to the instrument cart 14 via an interface cable 22*b*. In some cases, transmission can be wireless and interface cable 22*b* may not be present. The input device 22 can include right and left-hand controls (not shown) and/or foot pedals (not shown), which are moved/operated to produce input signals at the input device 22 and/or to control robotic surgical system 10. The instrument cart 14 can include a slave processor circuit 20*a* that receives and the control signals from the master processor circuit 22*a* and produces slave control signals operable to control the various surgical instrument systems 50 (and surgical instruments 60 thereof) during a surgical procedure. The workstation 12 can also include a user interface, such as a display (not shown) in communication with the master processor circuit 22*a* for displaying information (such as, body cavity images) for a region or site of interest (for example, a surgical site, a body cavity, or the like) and other information to a clinician. While both master and slave processor circuits are illustrated, in other aspects, a single processor circuit may be used to perform both master and slave functions.

Figure 29:
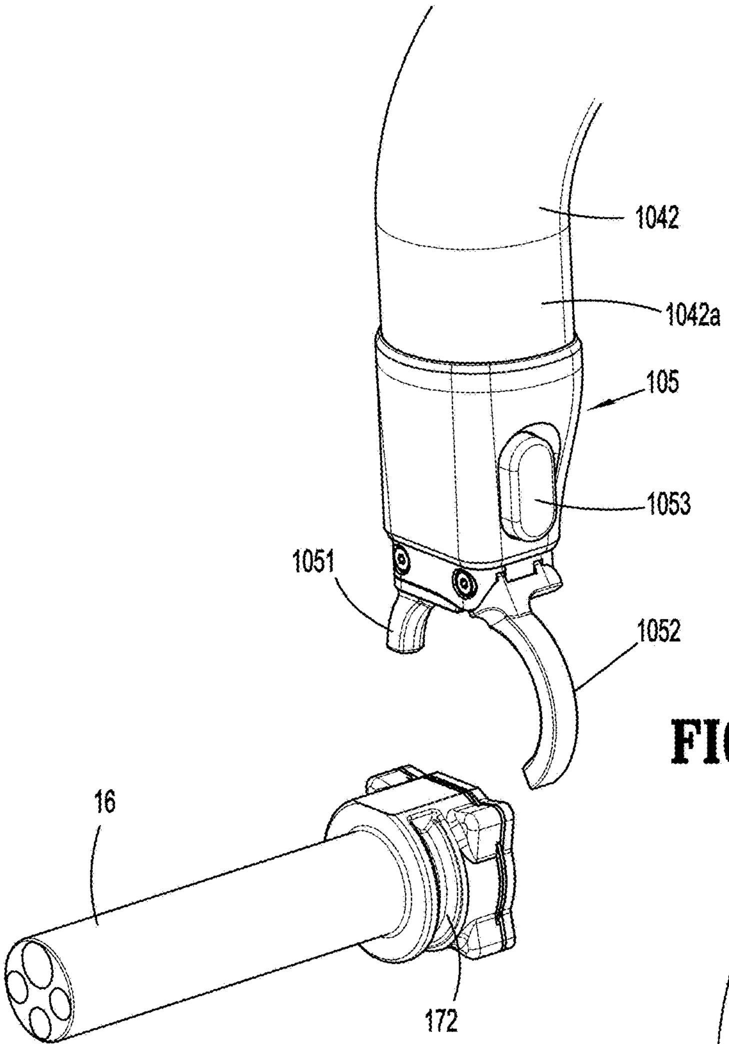
FIGS. 29-30 are progressive views illustrating the surgical porta assembly of FIG. 1A being secured to a port latch assembly of the control drive unit of FIG. 3.
Figure 30:
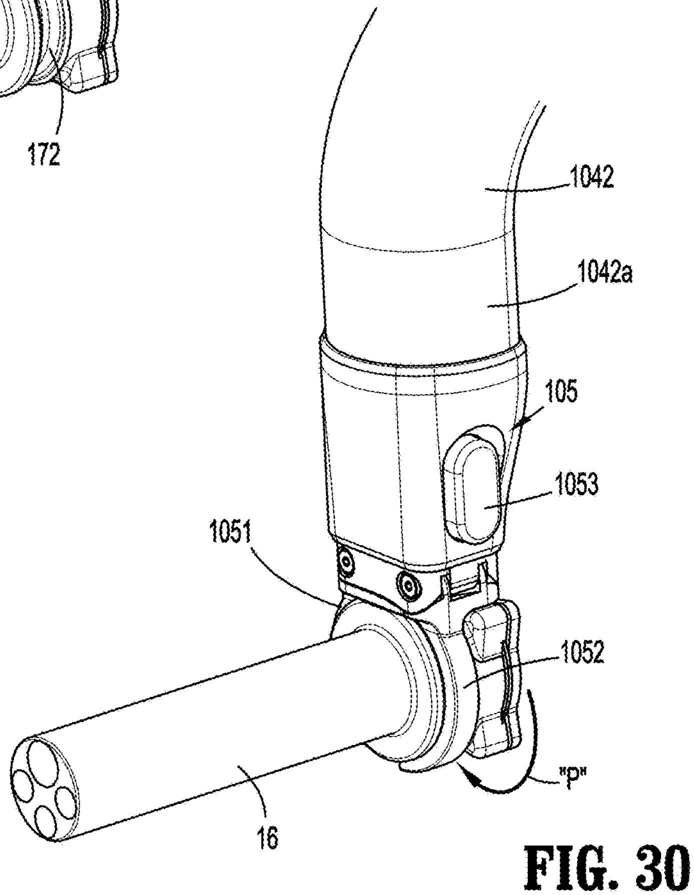

Turning now to FIGS. 2A, 2B, 3, 29 and 30 control drive assembly 100 is pivotably mounted to setup arm assembly 15. Control drive unit 101 of control drive assembly 100 includes a housing 102 that supports instrument drive assembly 103, including instrument drive units 103*a* (e.g., three) and endoscope drive unit 103*b*. Control drive unit 101 further includes a support bar assembly 104 that is mounted to housing 102. Support bar assembly 104 may have a hollow construction configured to enable internal wiring and weight reduction. Setup arm assembly 15 includes a first control pad 15*a* having buttons 15L, 15R, 15C, and 15E that are selectively actuatable to cause linear translation of respective ones of instrument drive and endoscope drive units 103*a*, 103*b* relative to control drive unit 101 as indicated by arrows "A" shown in FIG. 3. First control pad 15*a* further includes a cleaning button 15X. Housing 102 also supports a second control pad 15*b* that is on the opposite side of first control pad 15*a* but similarly includes buttons 15L, 15R, 15C, 15E, and 15X that likewise provide the same functions as the corresponding buttons on the first control pad 15*a*. Support bar assembly 104 includes a first portion 1041 including a rear bar 104*a* having a U-shaped configuration that extends around sidewalls of a proximal portion of housing 102 and beneath housing 102, and a second portion 1042 having handles 104*b*, and a port arm 104*c* that extends from handles 104*b* distally to port latch assembly 105 on a distal end portion of port arm 104*c*. First and second portions 1041 and 1042 are coupled together via rigid support bar joints 1043, which may be in the form of a dovetail clamp and joint to enable cable management, and service removal of first and/or second portions 1014, 1042. Port arm 104*c* has an arched configuration and extends to a float 1042*a* on a proximal end portion of port latch assembly 105 to enable post manufacturing alignment of port latch assembly 105 and to help mitigate any assembly stack up errors. Port latch assembly 105 includes a pivotable clamp arm 1051, a fixed clamp arm 1052, and an actuator 1053 operatively coupled to pivotable clamp arm 1051. In response to actuation of actuator 1053, pivotable clamp arm 1051 is pivotably movable relative to fixed clamp arm 1052, as indicated by arrows "P", to selectively couple to proximal housing 17*a* of surgical portal assembly 16 as illustrated in FIGS. 29 and 30. Pivotable clamp arm 1051 is selectively receivable within second annular channel 172 of proximal housing 17*a* of surgical portal assembly 16 and fixed clamp arm 1052 of port latch assembly 105 is receivable with first annular channel 171 of proximal housing 17*a* of surgical portal assembly 16. Port latch assembly 105 may be adjusted for alignment to instruments. Support bar assembly 104 further includes a plurality of brake release buttons 104*e* on inner facing surfaces of rear bar 104*a*, handles 104*b*, and port arm 104*c* of support bar assembly 104 that are configured to stop linear movement of instrument drive and/or endoscope drive units 103*a*, 103*b* relative to control drive unit 101. Brake release buttons 104*e* can be configured with illuminated activation.

With reference to FIGS. 4-7, control drive unit 101 includes a chassis assembly 106 and a leadscrew assembly 108 mounted to chassis assembly 106. Chassis assembly 106 includes a rear chassis 106*a*, a front chassis 106*b*, a spine box assembly 106*c*, and a chassis arm 106*d*. Spine box assembly 106*c* and chassis arm 106*d* connect rear and front chassis 106*a*, 106*b* together. Rear chassis 106*a* includes clamps 106*e* that center instrument and endoscope drive units 103*a*, 103*b* about spine box assembly 106*c* and support Z-axis driver boards (not shown). Front chassis 106*b* transfers load to single sided pitch joint and adds torsional stiffness for port arm 104*c* related loads (e.g., instrument trocar ("IT")). Lead screw assembly 108 includes leadscrews 109 supported in spine box assembly 106*c* and a drive assembly 110 supported on rear chassis 106*a*. Drive assembly 110 includes drivers (e.g., belts) 110*a*, drive gears 110*b*, idler gears 110*c*, leadscrew drivetrain motors 110*d* that cooperate to impart rotational force to lead screws 109 as drivers 110*a* rotate about drive gears 110*b*, as indicated by arrows "B", in response to actuation of leadscrew drivetrain motors 110*d*. Although shown as a belt drive system, drive assembly 110 may be any suitable drive system such as a chain drive, gear drive, cable drive, etc.

Figure 9:
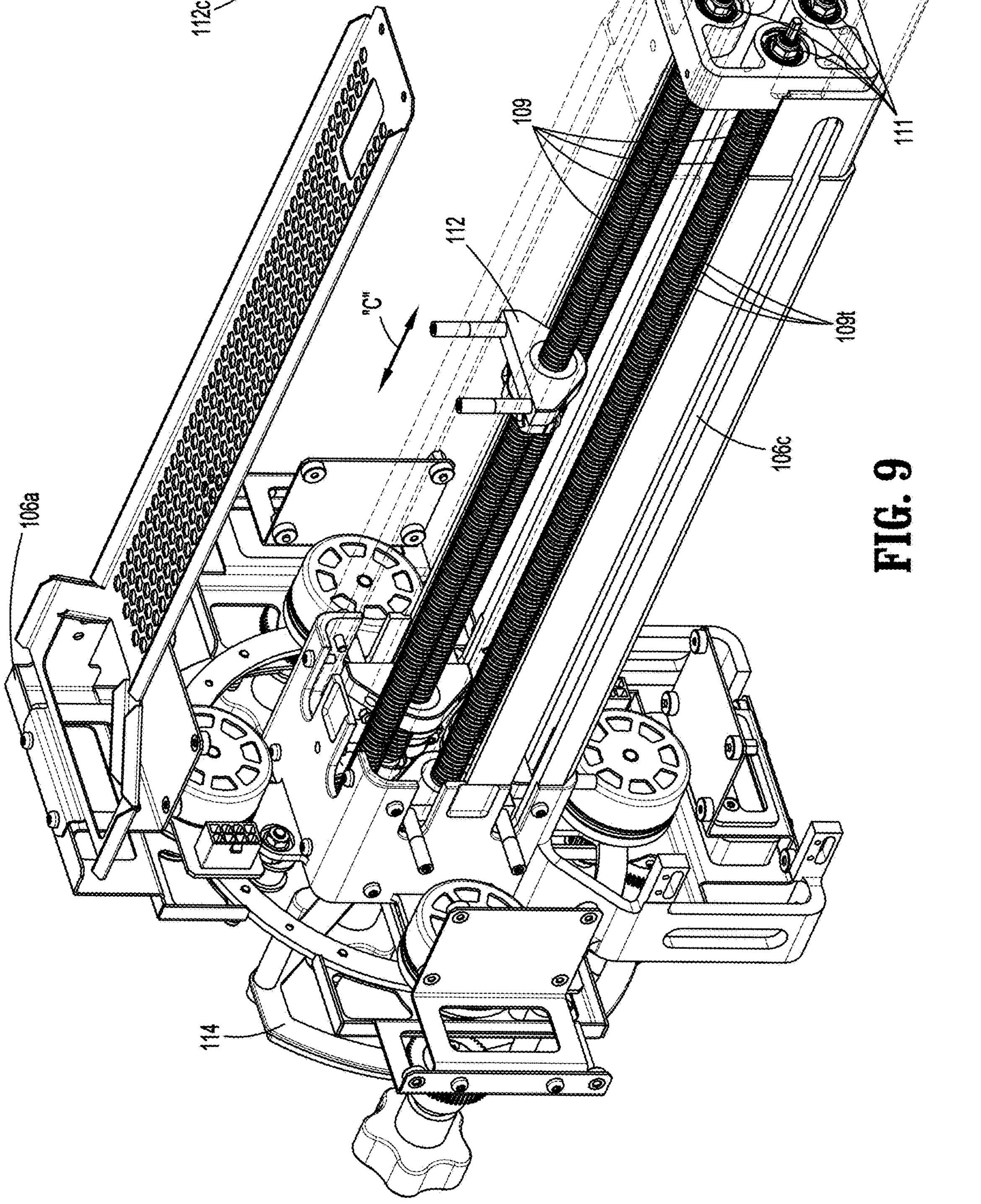
FIG. 9 is a view of FIG. 6 with a slide plate assembly of the leadscrew assembly of FIG. 4 shown in an advanced position and with a spine box assembly of the chassis assembly shown in phantom for clarity.

Drive assembly 110 of control drive unit 101 includes a plurality of independent drive subassemblies 1101, 1102, 1103, 1104, each of which is driven by a respective one of the drivers 110*a* and a respective one of the leadscrew drivetrain motors 110*d*. Drive assembly 110 further includes slide plate assemblies 112 that are movably mounted on leadscrews 109 (e.g., threadedly coupled thereto). Each slide plate assembly 112 is positioned to axially move along a respective one of the leadscrews 109, as indicated by arrows "C" shown in FIG. 9, in response to rotation of the respective leadscrew 109 to longitudinally translate instrument and/or endoscope drive units 103*a*, 103*b* relative to control drive unit 101.

Figure 8:
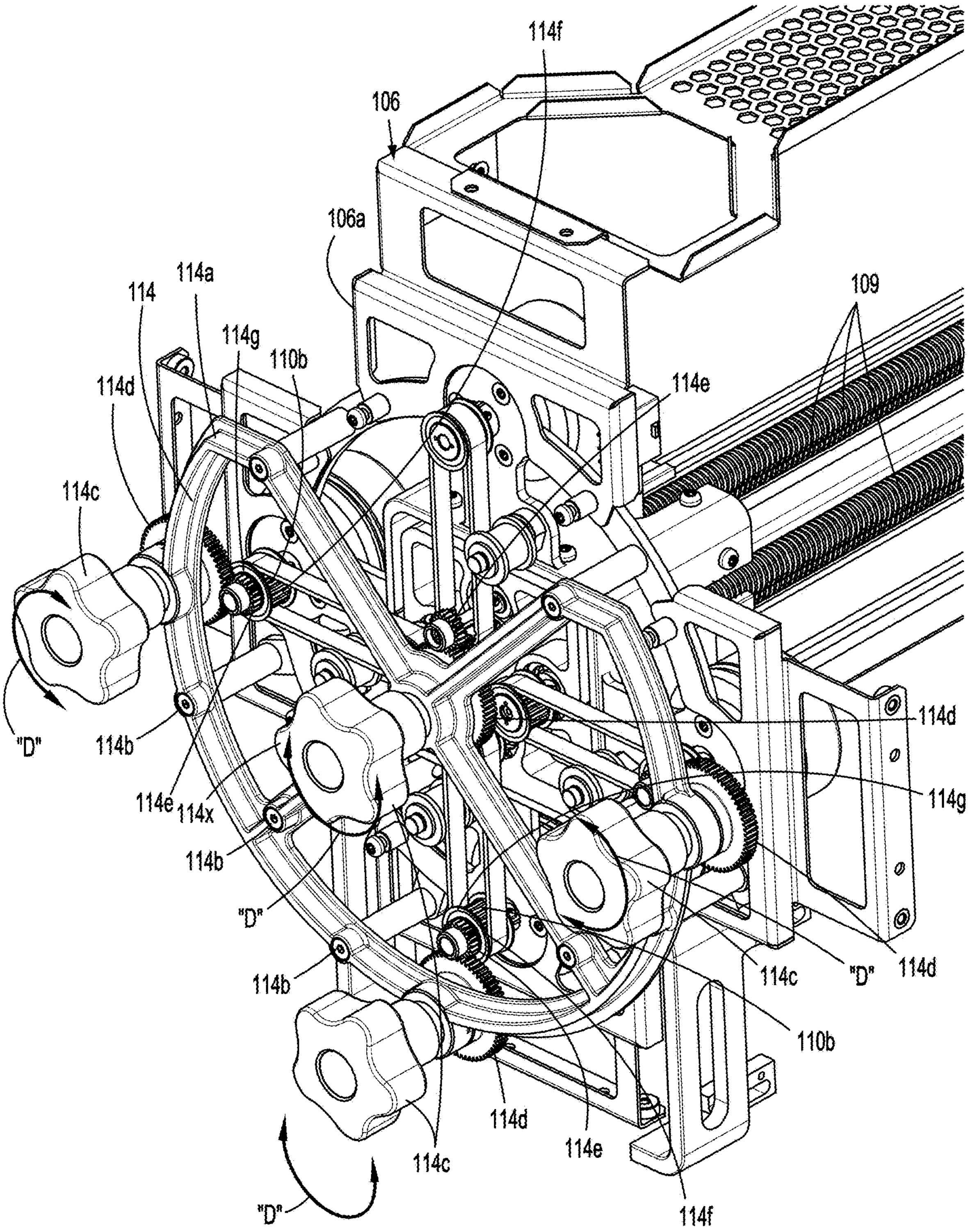
FIG. 8 is an enlarged, rear, perspective view of a proximal portion of FIG. 6.

Briefly, as seen in FIG. 8, rear chassis 106*a* of chassis assembly 106 further supports a manual release assembly (e.g., Z-axis) 114 having a mounting frame 114*a* secured to rear chassis 106*a* via fasteners 114*b*. Manual release assembly 114 further includes release knobs 114*c*, 114*x* with star handles that are manually rotatable, as indicated by arrows "D", and release gears or clutches 114*d* that are coupled to release knobs 114*c*, 114*x*. Release gears 114*d* are enmeshed with proximal portions or spur gears 114*e* of drive gears 110*b* of drive assembly 110 that are separated from distal portions 114*f* of drive gears 110*b* by an annulus 114*g*. Release gears 114*d* cooperate with spur gears 114*e* (e.g., 3:1 rotational advantage) to manually rotate leadscrews 109 when release knobs 114*c* are rotated for manually causing slide plate assemblies 112 to translate along leadscrews 109 for longitudinally translating instrument and/or endoscope drive units 103*a*, 103*b* relative to control drive unit 101. Release knobs 114*c*, 114*x* may be positioned relative to one another to enable simultaneous, multi axes retraction (e.g., 2 axes). Release knob 114*x* is centrally positioned on mounting frame 114*a* to increase clearance around critical clash conditions with setup arm assembly 15.

Figure 10:
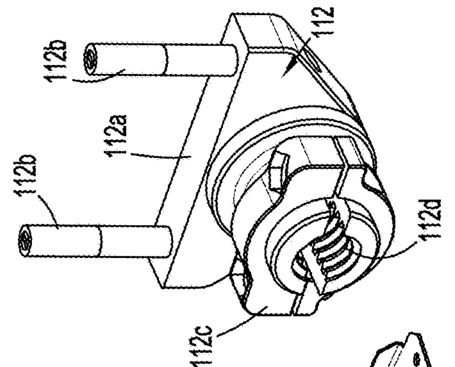
FIG. 10 is an enlarged, perspective view of one of the slide plate assemblies of the leadscrew assembly shown in FIG. 9.
Figure 11:
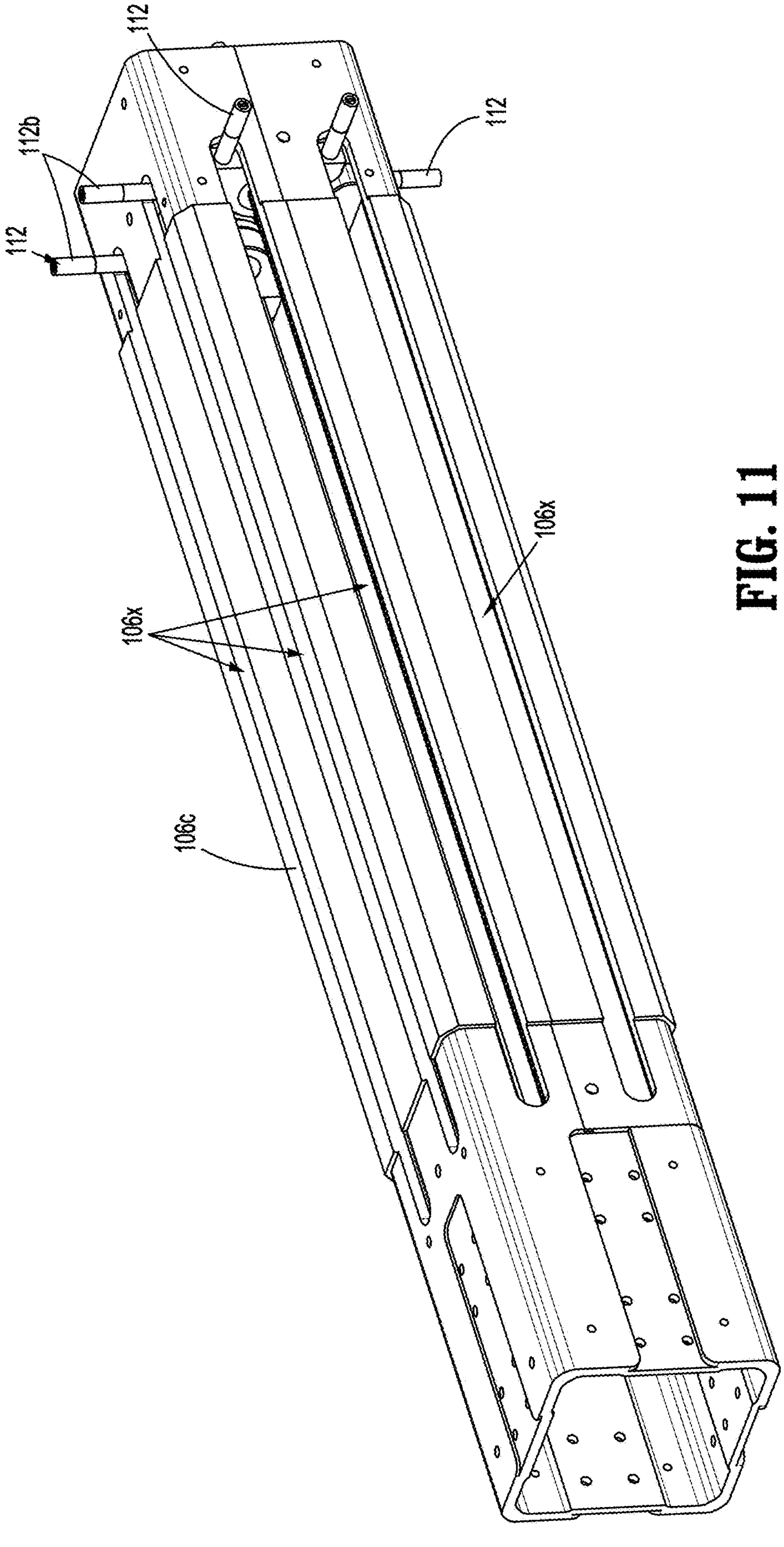
FIG. 11 is an enlarged, perspective view of the spine box assembly of FIG. 9 shown with the slide plate assemblies disposed in a retracted position within the spine box assembly.
Figure 12:
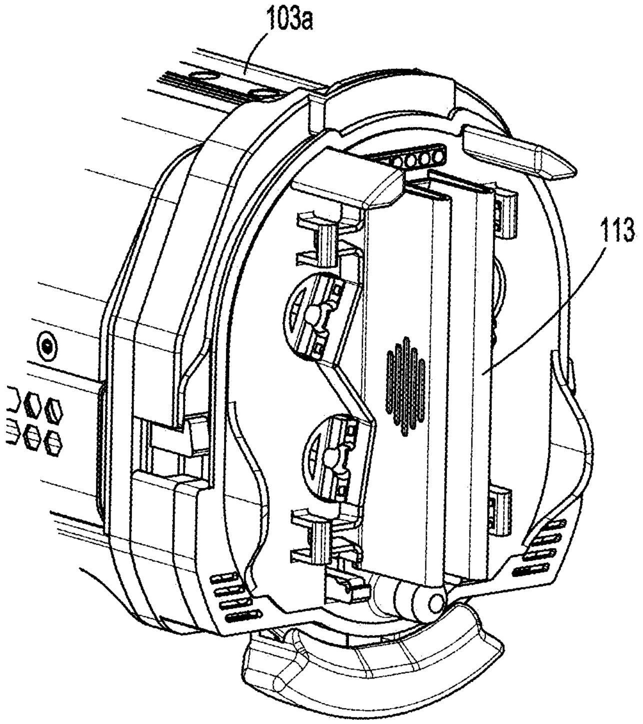
FIG. 12 is an enlarged, perspective view of the indicated area of detail shown in FIG. 3 and illustrating an instrument dog drive alignment tool secured to a distal end portion of an instrument drive unit of the control drive unit of FIG. 3.

With reference to FIGS. 10-11, each slide plate assembly 112 includes a slide plate 112*a* having drive pins 112*b* extending therefrom for engagement with instrument and/or endoscope drive units 103*a*, 103*b*. Slide plate 112*a* further supports an anti-backlash nut 112*c* with internal threading 112*d* that threadedly engages threads 109*t* of one of the respective leadscrews 109. Leadscrews 109 are supported in spinebox assembly 106*c* by bearings 111 that may be configured to enable retraction speeds of leadscrews 109 greater than 200 mm/s, for example. Spinebox assembly 106*c* defines a plurality of drive pin channels 106*x* that extend longitudinally along a majority of a length of spinebox assembly 106*c* and receive drive pins 112*b* of slide plate assemblies 112 therethrough.

Figure 13:
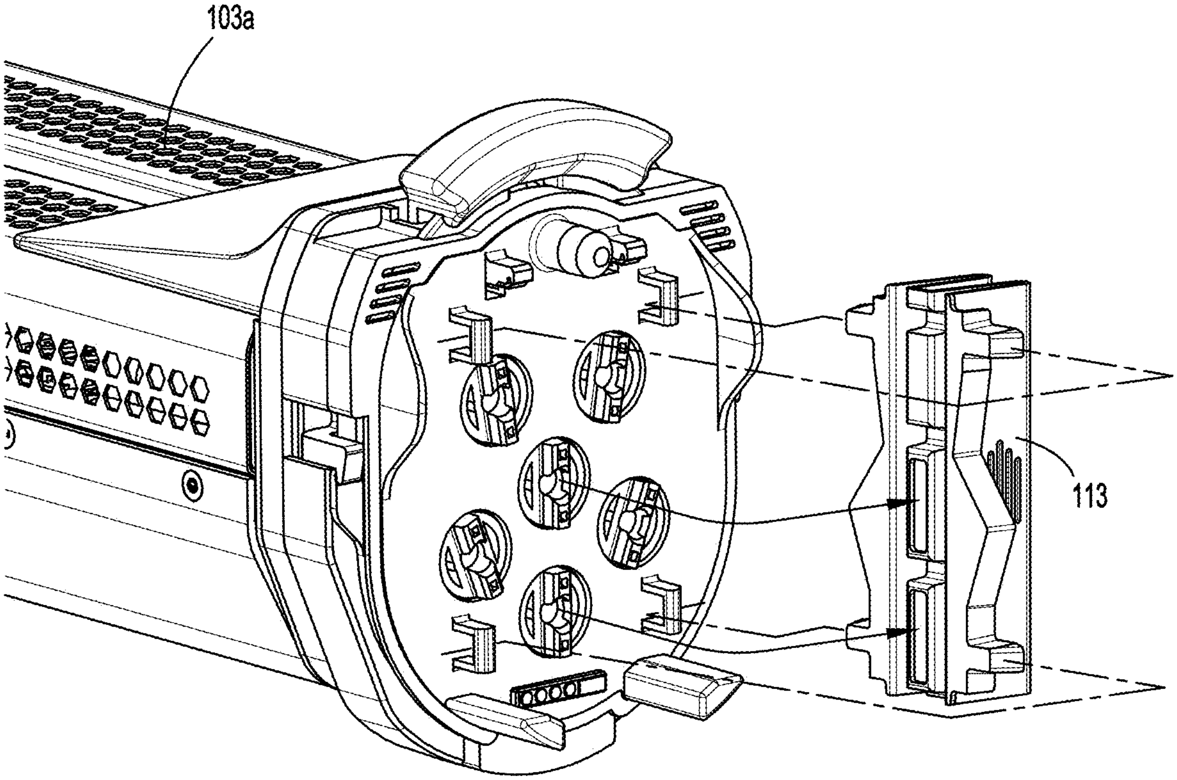
FIG. 13 is a perspective view illustrating the instrument dog drive alignment tool of FIG. 12 being removed from the distal end portion of the instrument drive unit of FIG. 12.
Figure 14:
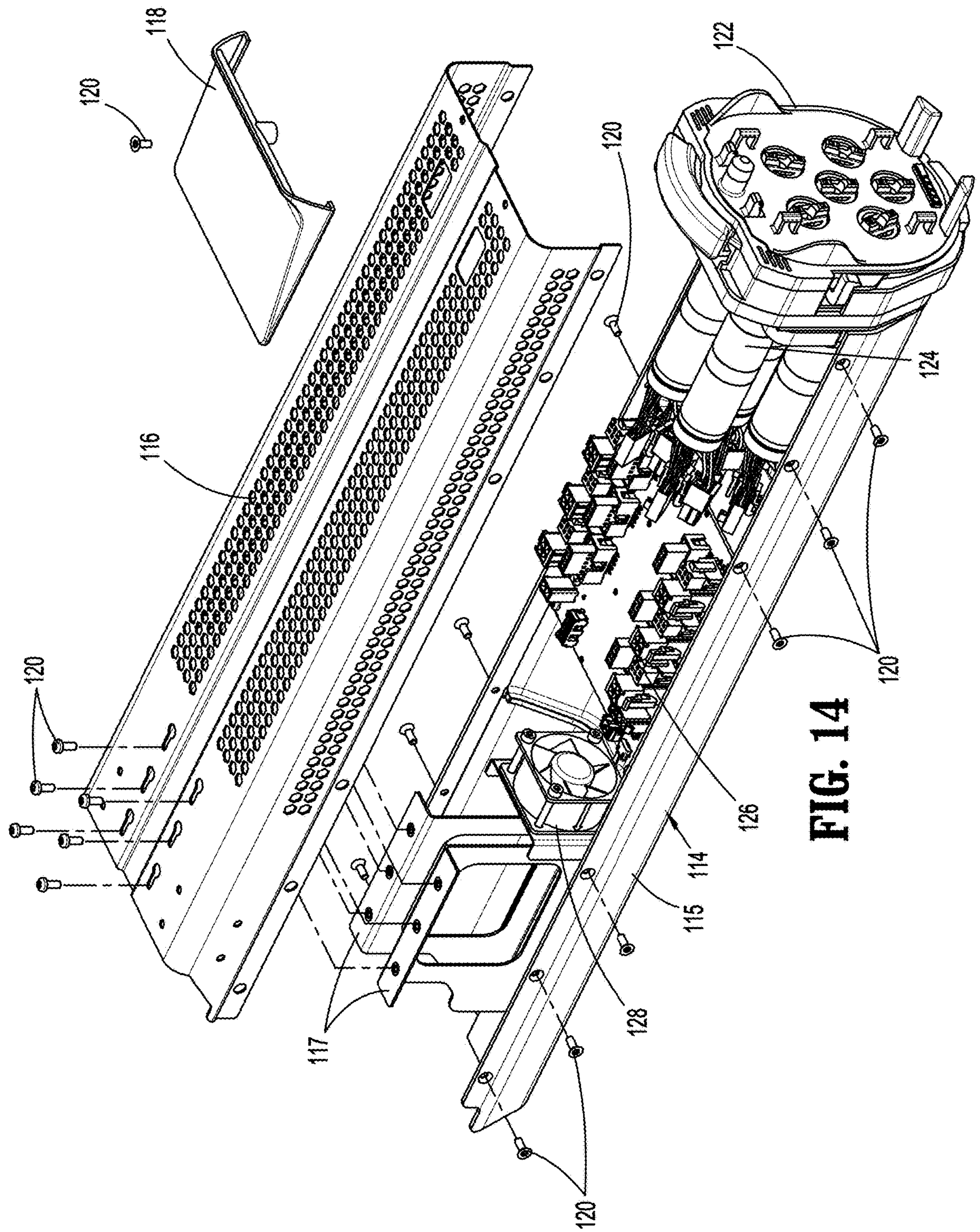
FIG. 14 is a front, perspective view, with parts separated, of an instrument drive unit of the control drive unit of FIG. 3.
Figure 15:
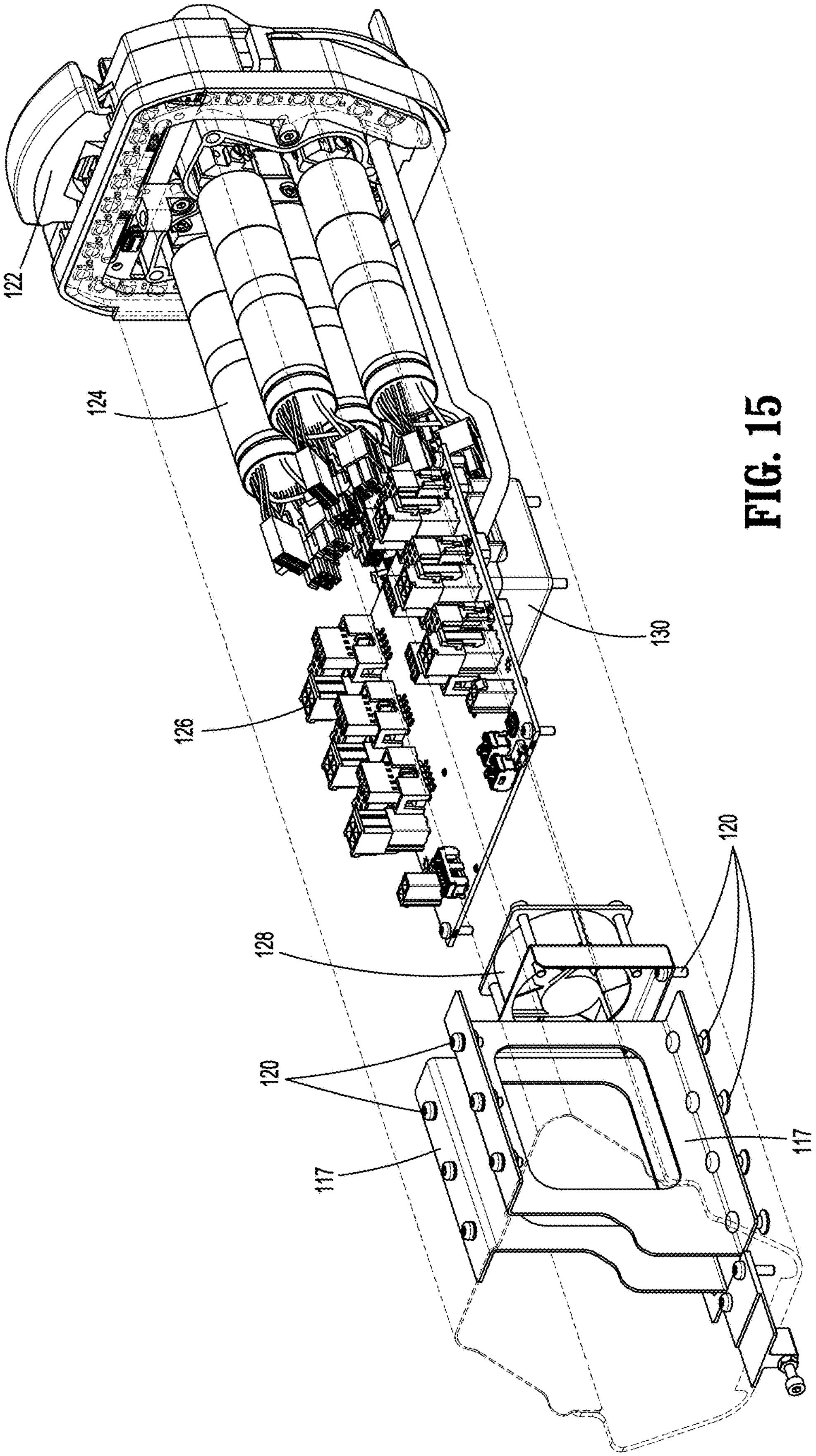
FIG. 15 is a rear, perspective view of the instrument drive unit of FIG. 14 with portions thereof removed or shown in phantom for clarity.
Figure 16:
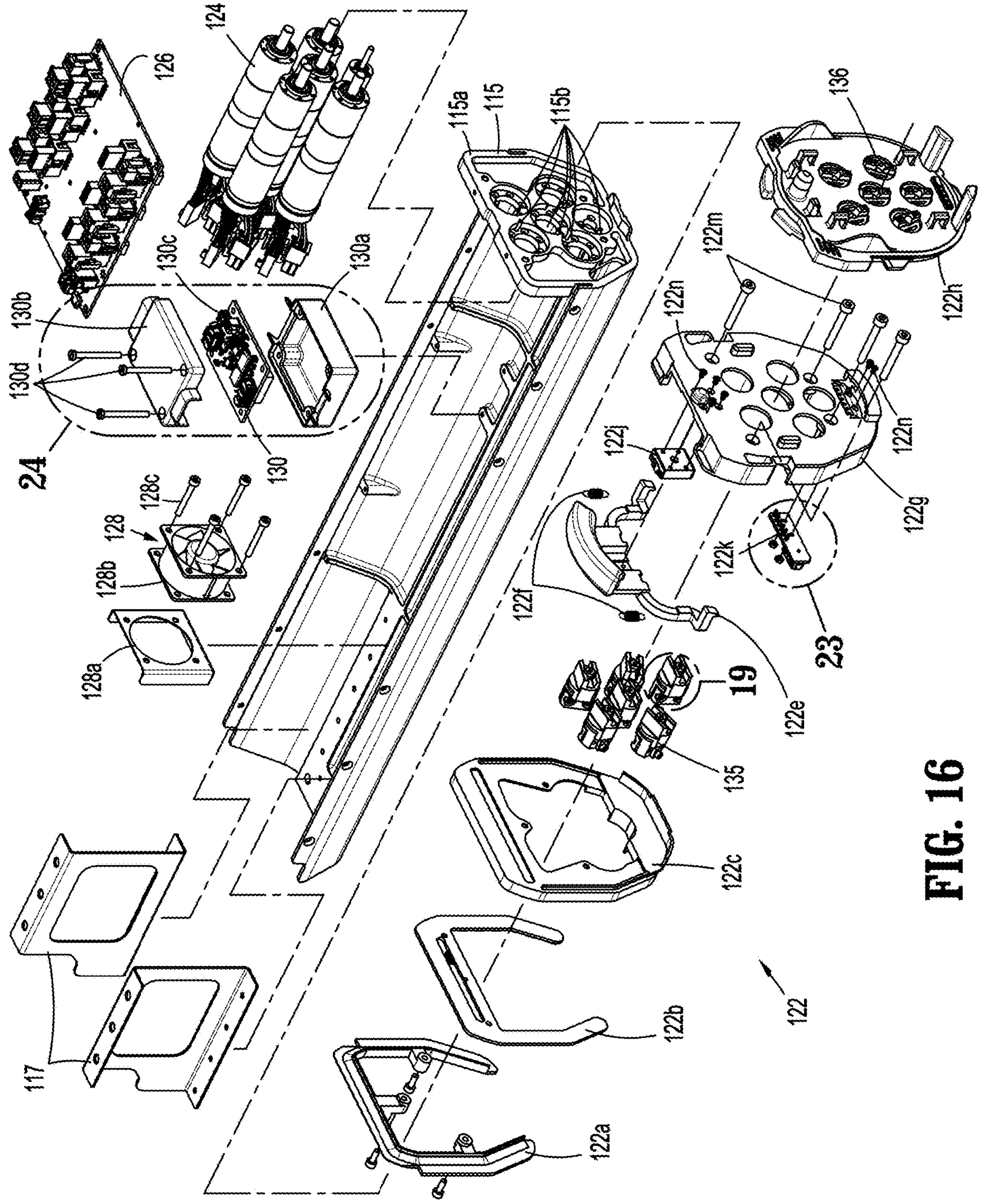
FIG. 16 is a front, perspective view, with parts separated, of portions of the instrument drive unit of FIG. 14.

Turning now to FIGS. 12-23, instrument drive unit 103*a* supports an instrument drive dog alignment tool 113 that is configured to pre-align drive dogs of instrument drive unit 103*a*. Instrument drive dog alignment tool 113 is selectively removable as shown in FIG. 13 to enable surgical instruments 26 to be attached to instrument drive unit 103*a*.

With reference to FIGS. 14-16 and 21-23, instrument drive unit 103*a* of control drive unit 101 includes a shroud assembly 114 including a lower shroud 115, an upper shroud 116, support plates 117, and a scoop 118 that are coupled together by fasteners 120. Shroud assembly 114 may function to provide an isolation barrier. Lower shroud 115 extends distally to a motor mount face 115*a* having hard stop pins 115*b* projecting therefrom. Instrument drive unit 103*a* includes an instrument coupling assembly 122 supported on a distal end portion of shroud assembly 114. Instrument drive unit 103*a* supports a motor assembly 124, a control board assembly 126, a cooling board assembly 128, and an isolation board assembly 130. Cooling board assembly 128 includes a mounting bracket 128*a* and a fan 128*b* that are secured together by fasteners 128*c* and mounted to lower shroud 115 by fasteners 120. Isolation board assembly 130 includes a lower housing 130*a* and an upper housing 130*b* that supports an isolation board 130*c* therebetween and are secured together by fasteners 130*d*. Instrument coupling assembly 122 includes an LED light ring reflector 122*a* that reflects light outwardly from LEDs 122*d*, an LED light ring 122*b* in the form of a printed circuit board having LEDs 122*d* mounted thereto, an LED light ring diffuser 122*c* that diffuses light from the LEDs 122*d*, a sterile adapter latch 122*e*, tension springs 122*f*, an IDU housing 122*g*, and an instrument sterile adapter assembly 122*h*. IDU housing 122*g* supports a linear slide 122*j* and an instrument ID board 122*k*. Instrument ID board 122*k* includes a plurality of pogo pins 1222 that extend therefrom and are engageable with instrument sterile adapter assembly 122*h*. Pogo pins 1222 are configured to detect connection of, for example, instrument sterile adapter assembly 122*h* and/or surgical instrument 26, provide a current limited low voltage supply to instrument logic, and/or provide I2C communication with a secure memory device. Fasteners 122*m*, 122*n* couple various components of instrument coupling assembly 122 together. Sterile adapter latch 122*e* functions to selectively lock instrument sterile adapter assembly 122*h* in position. Tension springs 122*f* enable sterile adapter latch 122*e* to move vertically (e.g., up) and return to a locked position from an unlocked position when sterile adapter latch 122*e* is actuated. Linear slide 122*j* enables smooth actuation of sterile adapter latch 122*e*. In aspects, coupling assembly 122 defines a 4-point locking system for securing instrument sterile adapter assembly 122*h* thereto and for ensuring instrument sterile adapter assembly 122*h* does not move when a surgical instrument 26 is fitted onto instrument sterile adapter assembly 122*h*.

Figure 17:
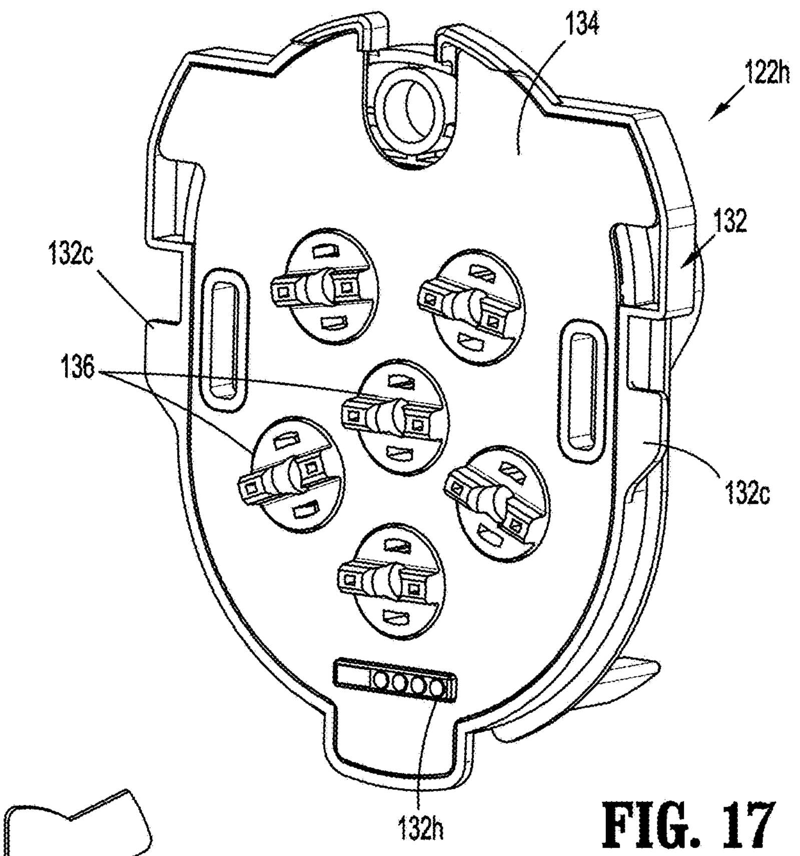
FIG. 17 is an enlarged, rear, perspective view of a sterile adapter assembly of the instrument drive unit of FIG. 14.
Figure 18:
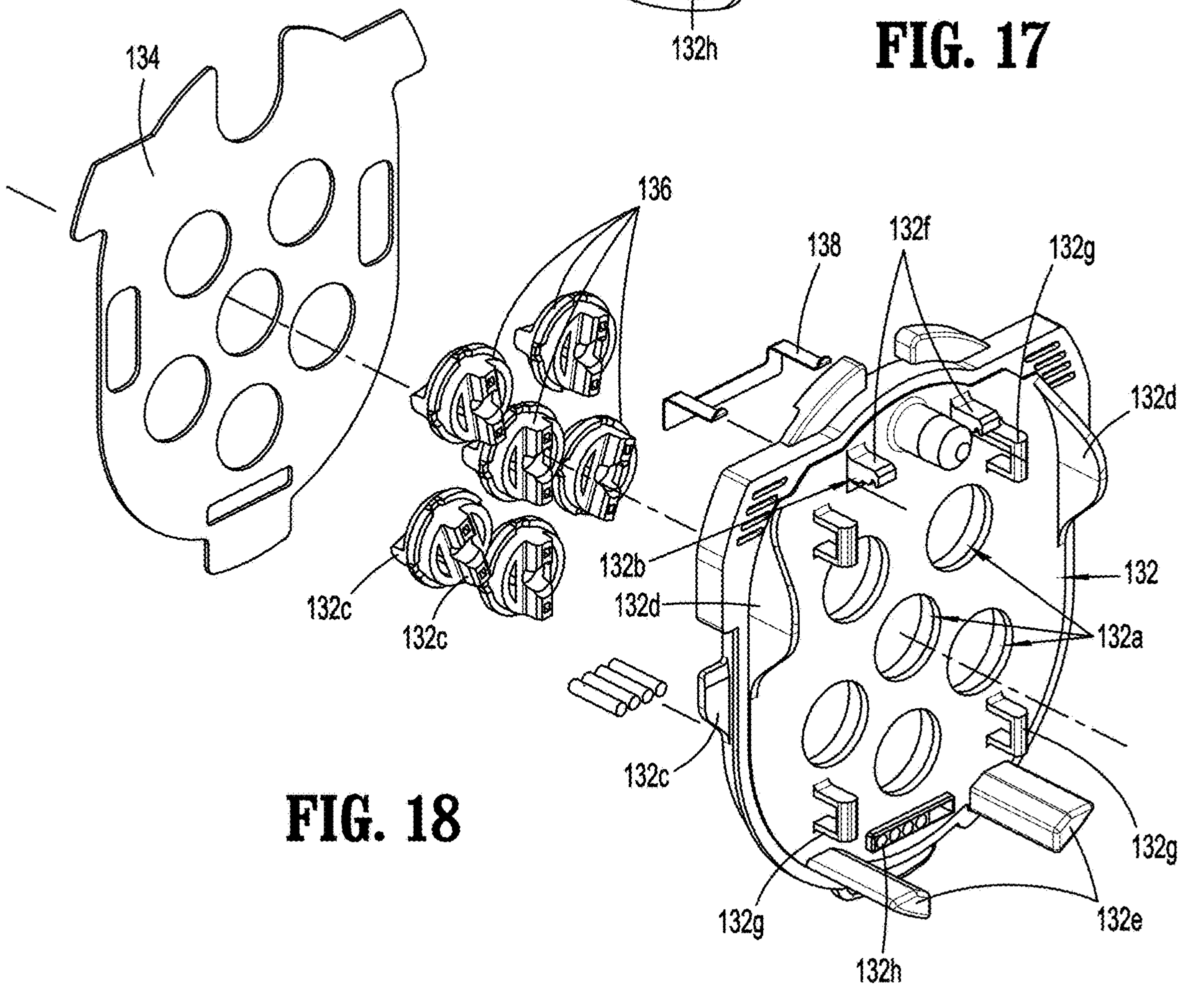
FIG. 18 is a front, perspective view, with parts separated, of the sterile adapter assembly of FIG. 17.

Referring to FIGS. 17 and 18, sterile adapter assembly 122*h* includes an adapter housing 132, a rear cover 134, drive dogs 136 (e.g., Oldham coupling style), and a clip 138. Adapter housing 132 defining coupler apertures 132*a* and clip openings 132*b* therethrough. Adapter housing 132 further includes latch wings 132*c* extending laterally therefrom and configured to engage sterile adapter latch 122*e*. Adapter housing 132 further includes guide wings 132*d*, lower proximal fingers 132*e*, upper proximal fingers 132*f*, and lock bars 132*g* for facilitating securement of proximal portions of surgical instruments 26 onto sterile adapter assembly 122*h*. Adapter housing 132 further includes an instrument ID board interface 132*h* for receiving instrument ID board 122*k*. Each drive dog 136 includes a proximal coupling 136*a* and a distal coupling 136*b*. In accordance with the disclosure, a surgical drape (not shown) is secured to adapter housing 132, via heat staking, adhering or the like, and is configured to extend over an entire length of endoscope drive unit 103*b* or instrument drive unit 103*a*, to thereby sheath endoscope drive unit 103*b* or instrument drive unit 103*a* during operation or use of control drive unit 101. It is envisioned that a surgical drape extends over each endoscope drive unit 103*b* or instrument drive unit 103*a*, that each surgical drape for each endoscope drive unit 103*b* or instrument drive unit 103*a* may be integrally formed with one another, and that a surgical drape assembly may be provided which includes a surgical drape for each endoscope drive unit 103*b* or instrument drive unit 103*a*, for support bar assembly 104, and for control drive unit 101.

Figure 19:
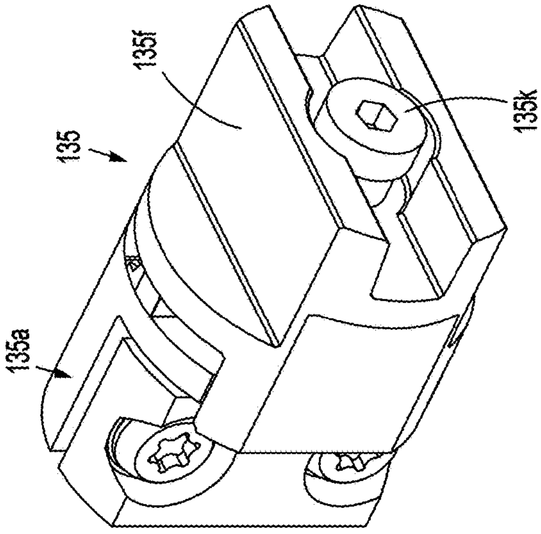
FIG. 19 is an enlarged, perspective view of a drive dog assembly of the instrument drive unit of FIG. 14.
Figure 20:
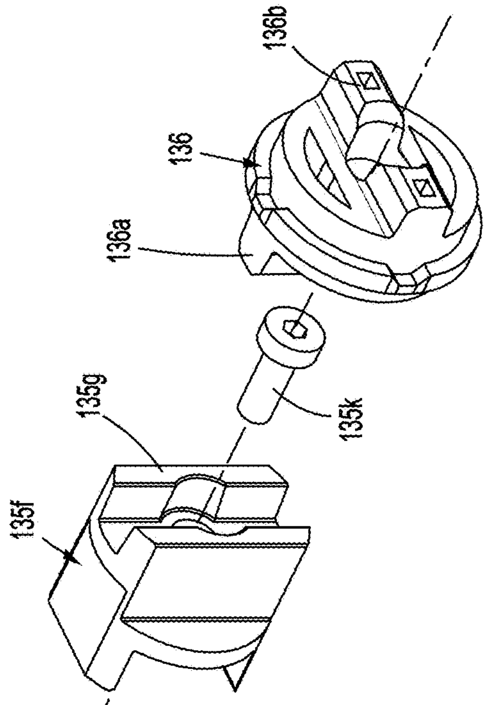
FIG. 20 is a reduced, perspective view, with parts separated, of the drive dog assembly of FIG. 19 shown in relation to a distal portion of a motor of the instrument drive unit of FIG. 14.
Figure 20:
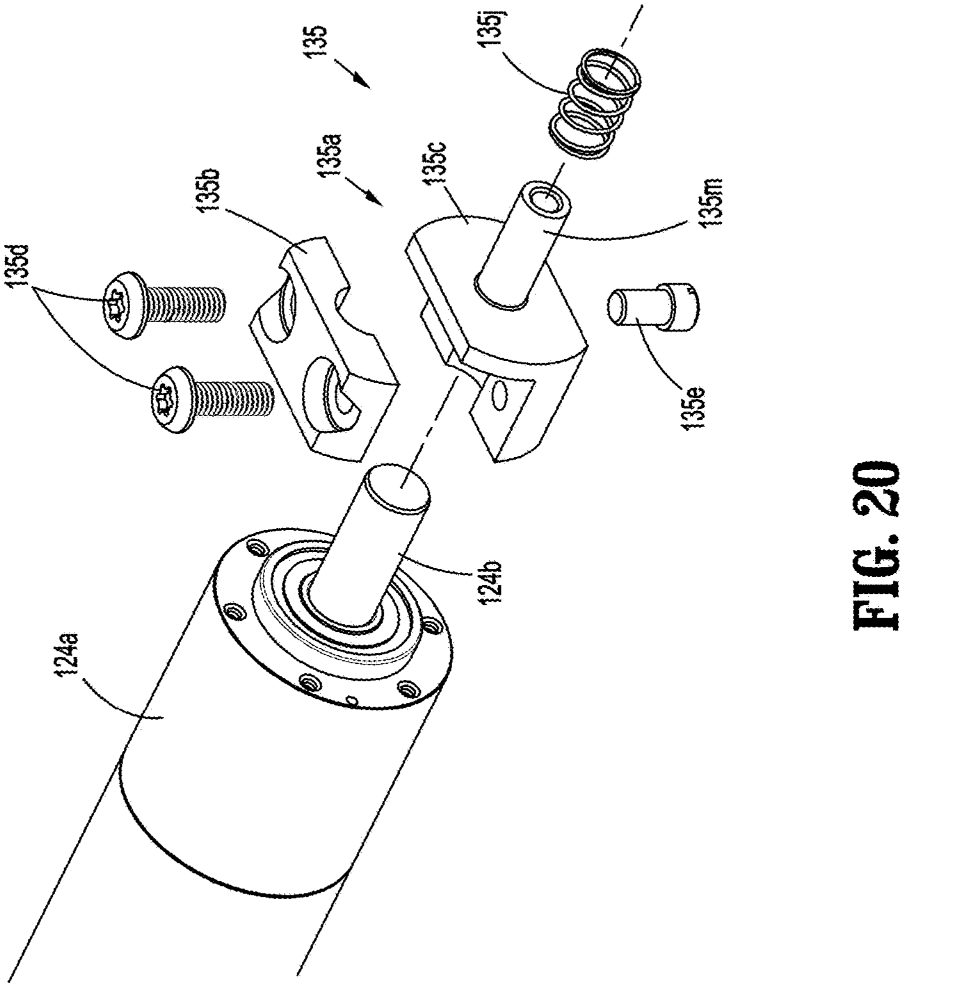
Figure 21:
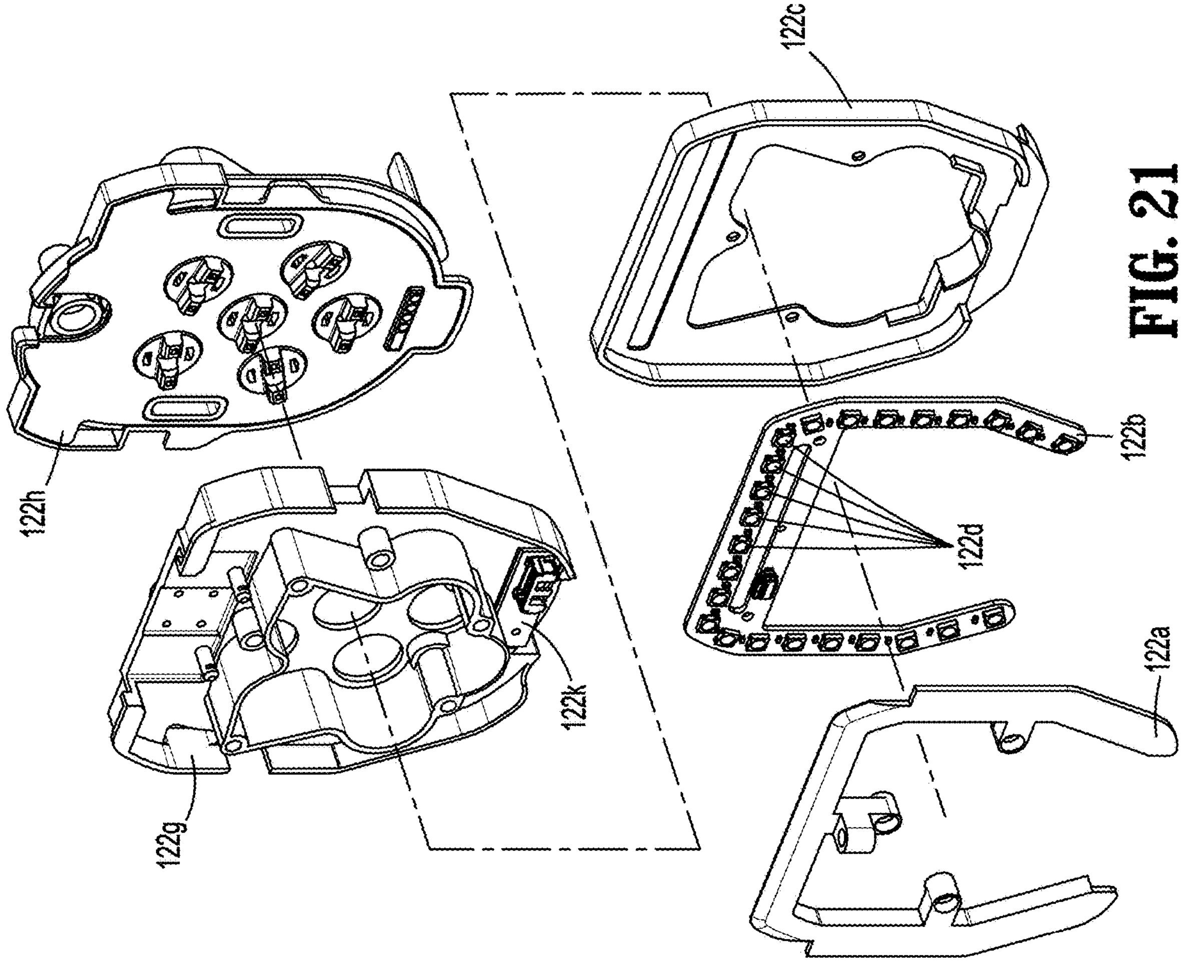
FIG. 21 is an enlarged, perspective view, with parts separated of a distal end portion of the instrument drive unit of FIG. 14.
Figure 22:
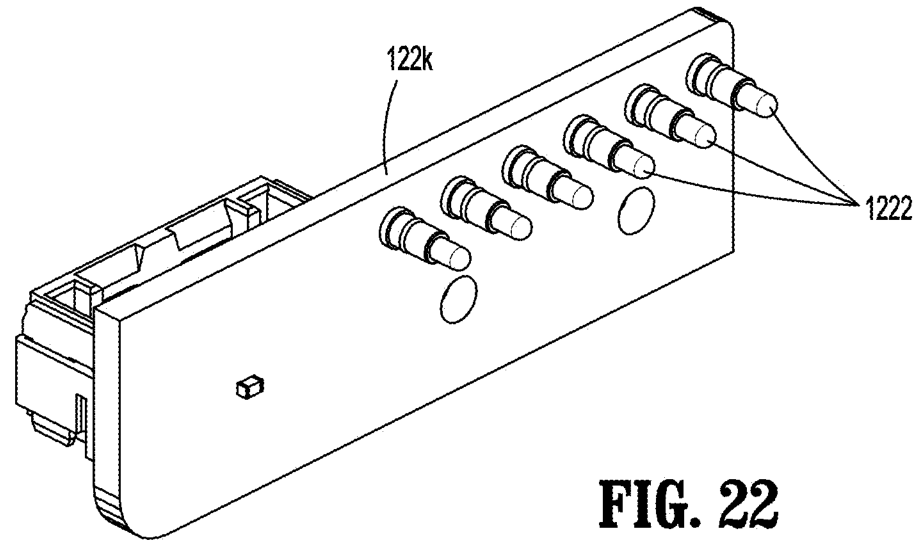
FIG. 22 is an enlarged, perspective view of an instrument ID board of the instrument drive unit of FIG. 14.
Figure 23:
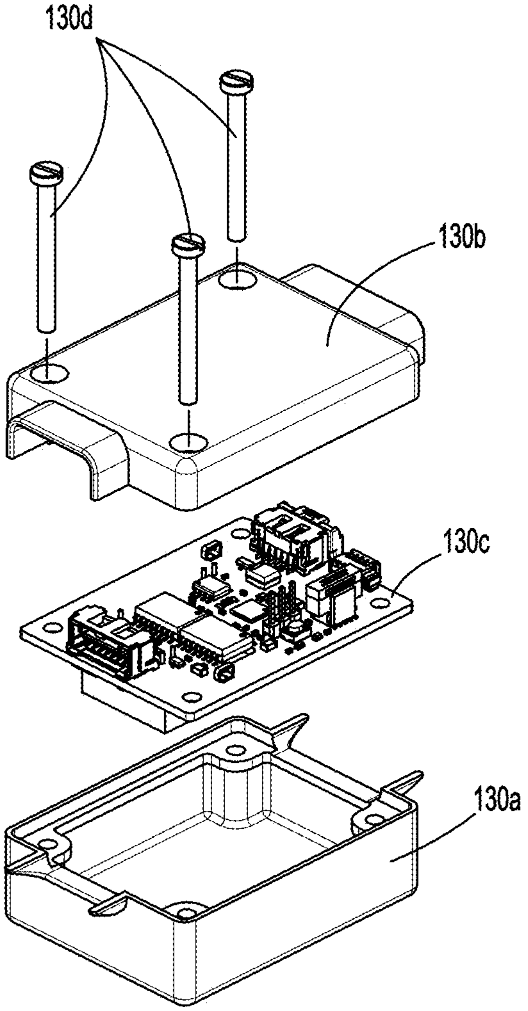
FIG. 23 is an enlarged, perspective view of an IDU isolation board assembly of the instrument drive unit of FIG. 14.
Figure 24:
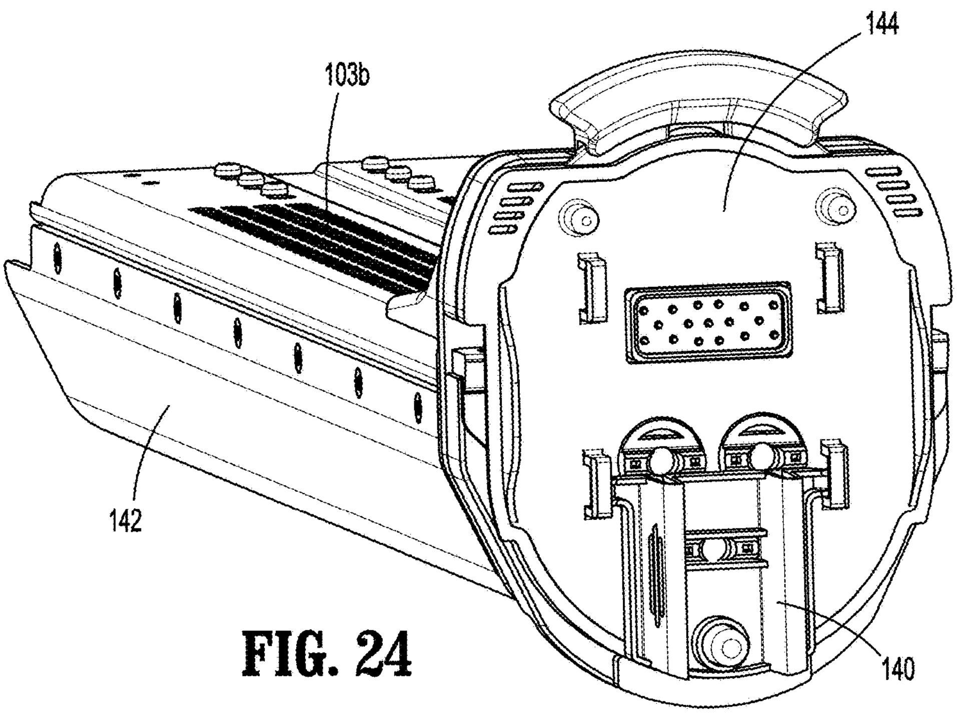
FIG. 24 is an enlarged, front, perspective view of an endoscope drive unit of the control drive unit of FIG. 3 with an endoscope dog drive alignment tool shown secured to a distal end portion of the endoscope drive unit.

With reference to FIGS. 19 and 20, each motor 124*a* of motor assembly 124 supports a drive dog drive assembly 135 that operably couples the respective motor 124*a* to a respective drive dog 136 of sterile adapter assembly 122*h*. Drive dog drive assembly 135 includes a clamp collar assembly 135*a* that locks onto a motor output shaft 124*b* of motor 124*a*. Clamp collar assembly 135*a* includes an upper collar 135*b* and a lower collar 135*c* that are secured together and onto motor output shaft 124*b* by fasteners 135*d* and set screw 135*e*. Set screw 135*e* is positioned to extend from clamp collar assembly 135*a* such that set screw 135*e* can engage with hard stop pins 115*a* of motor mount face 115*a* of lower shroud 115 to limit rotation of drive dog drive assembly 135. Drive dog drive assembly 135 further includes an output dog 135*f* that extends to a distal coupling 135*g* for engagement with proximal coupling 136*a* of drive dog 136. In aspects, distal coupling 135*g* may have any suitable taper, such as, for example, 4 degrees, to facilitate and interface with proximal coupling 136*a* of drive dog 136. Drive dog drive assembly 135 further includes a compression spring 135*j* (e.g., 2 newtons) that is selected to avoid high loading forces, to take up any axial clearance, and for enabling output dog 135*f* and drive dog 136 to maintain engagement. Drive dog drive assembly 135 further includes a screw 135*k* that secures output dog 135*f* to clamp collar assembly 135*a* via a threaded distal shaft 135*m* extending from lower collar 135*c*.

Figure 25:
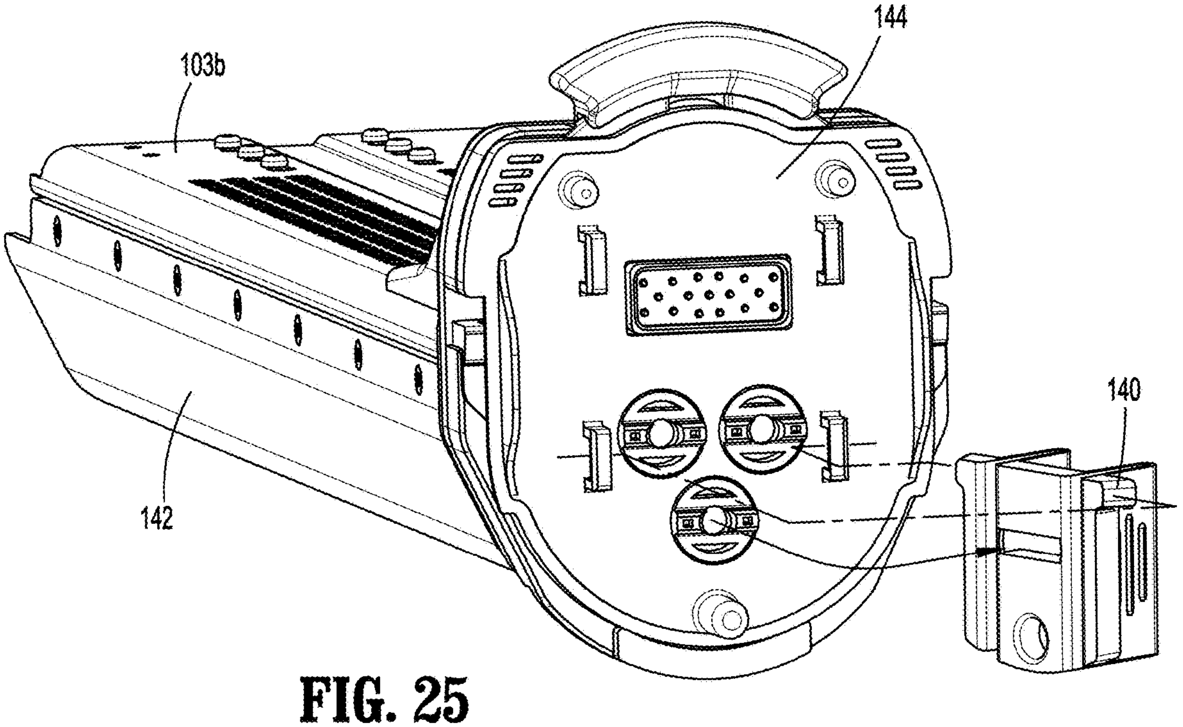
FIG. 25 is a front, perspective view of FIG. 24 with the endoscope dog drive alignment tool shown removed from the distal end portion of the endoscope drive unit.
Figures 26, 27:
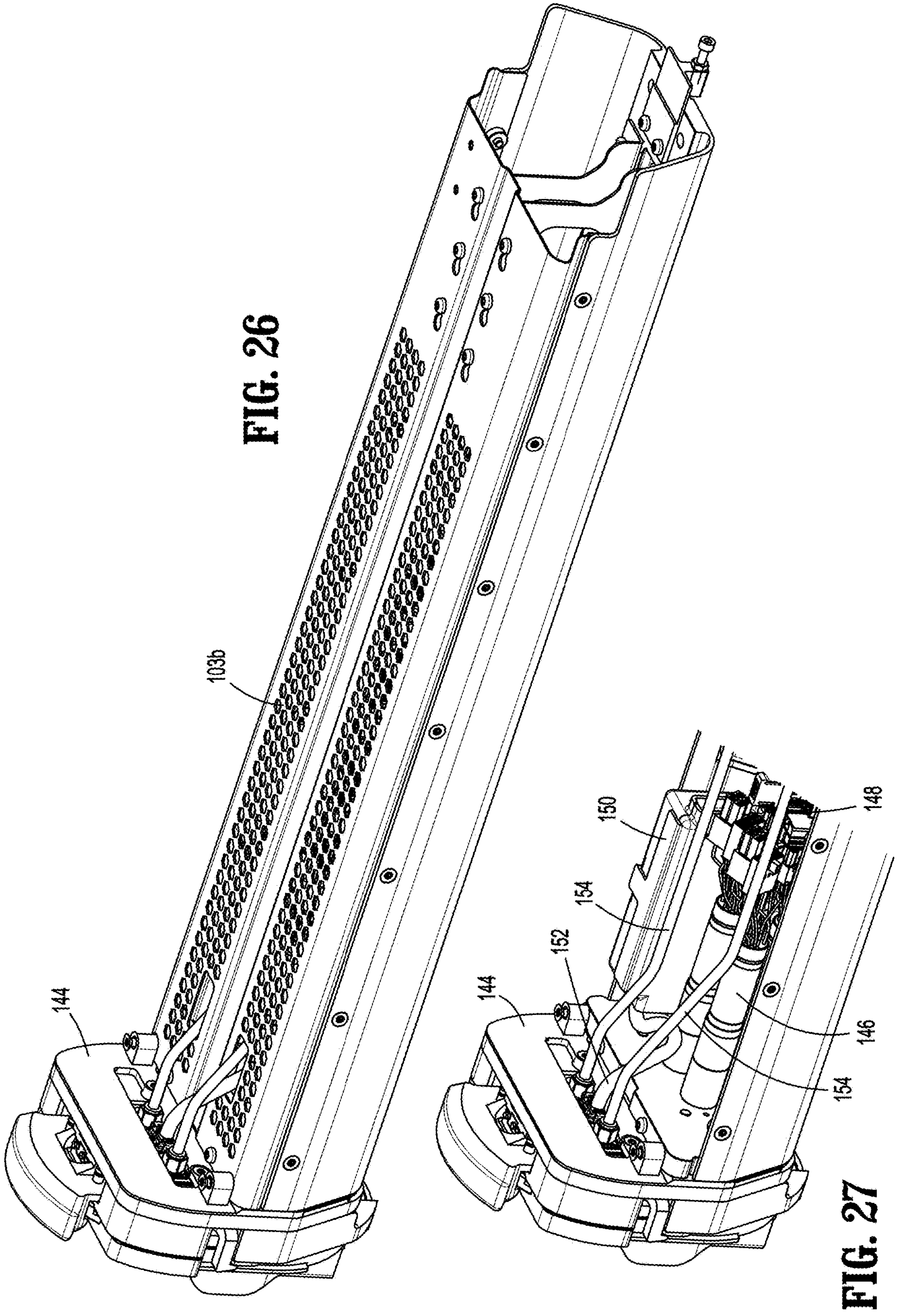
FIG. 26 is a rear, perspective view of the endoscope drive unit of FIG. 24.
FIG. 27 is a rear, perspective view of a distal end portion of the endoscope drive unit of FIG. 24, the distal end portion shown with portions thereof removed for clarity.
Figure 28:
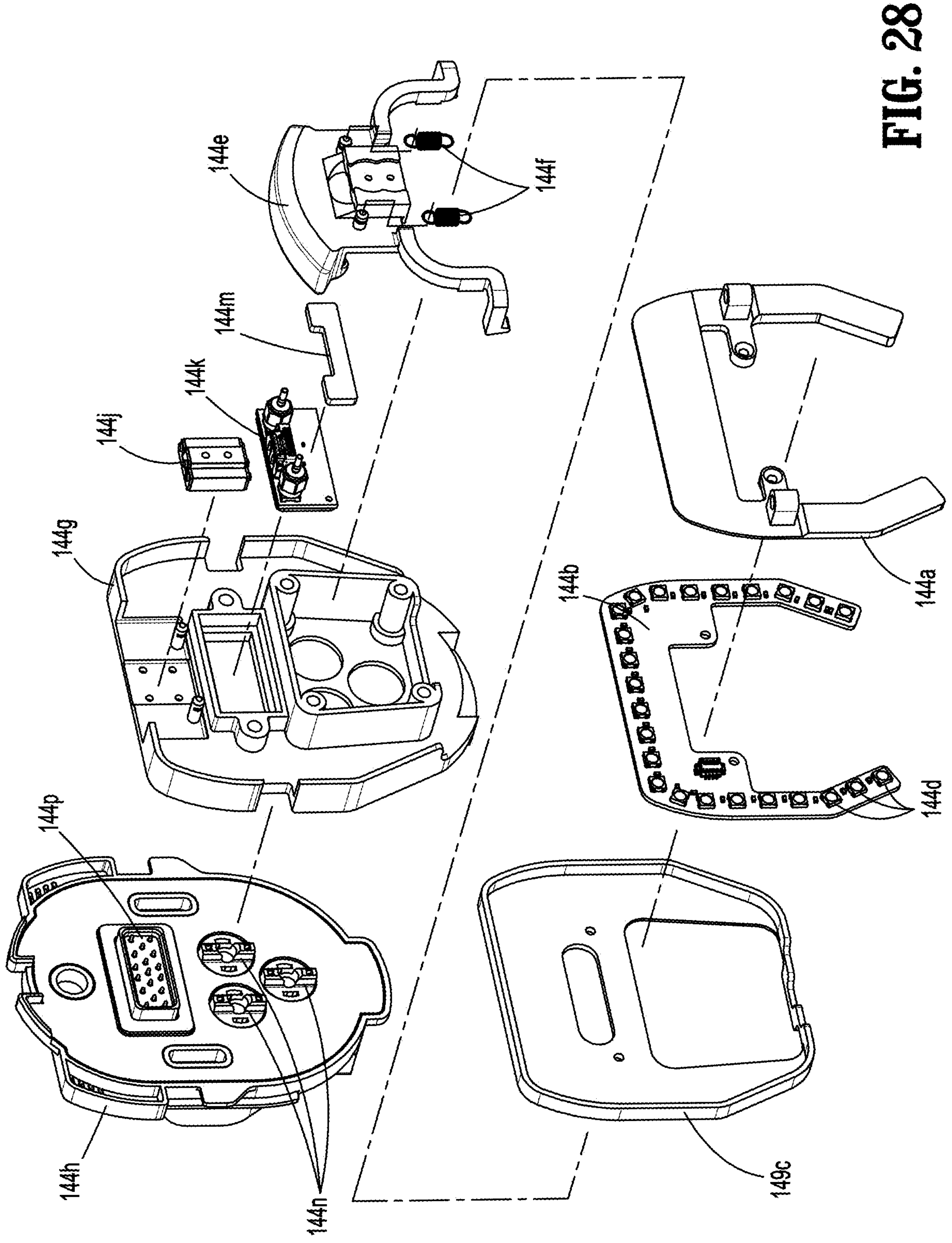
FIG. 28 is an enlarged, rear, perspective view, with parts separated, of a distal end portion of the endoscope drive unit of FIG. 24.

Turning now to FIGS. 24-28, endoscope drive unit 103*b* of control drive unit 101 is similar to instrument drive unit 103*a* and supports an endoscope drive dog alignment tool 140 that is configured to pre-align drive dogs of endoscope drive unit 103*b* and is selectively removable, as shown in FIG. 25, to enable endoscope 28 to be attached to endoscope drive unit 103*b*.

Endoscope drive unit 103*b* includes a shroud assembly 142 having an endoscope coupling assembly 144 supported on a distal end portion of shroud assembly 142. Shroud assembly 142 supports a motor assembly 146, a control board assembly 148, an endoscope isolation board assembly 150, a high-voltage domain connection 152, and video coax cables 154, and other components similar to instrument drive unit 103*b* such as a cooling board assembly.

Endoscope coupling assembly 144 of endoscope drive unit 103*b* includes an LED light ring reflector 144*a*, an LED light ring 144*b* in the form of a printed circuit board having LEDs 144*d* mounted thereto, an LED light ring diffuser 144*c* that diffuses light from the LEDs 144*d*, a sterile adapter latch 144*e*, tension springs 144*f*, an EDU housing 144*g*, and an endoscope sterile adapter assembly 144*h*. Endoscope coupling assembly 144 further includes a linear slide 144*j*, an endoscope connector board 144*k*, and a board gasket 144*m*. Endoscope connector board 144*k* couples to high-voltage domain connection 152 and video coax cables 154. Endoscope sterile adapter assembly 144*h* includes endoscope drive dogs 144*n* and a connector 144*p* (e.g., 17 pin) embedded in endoscope sterile adapter assembly 144*h* that couples with endoscope connector board 144*h*.

Figure 31:
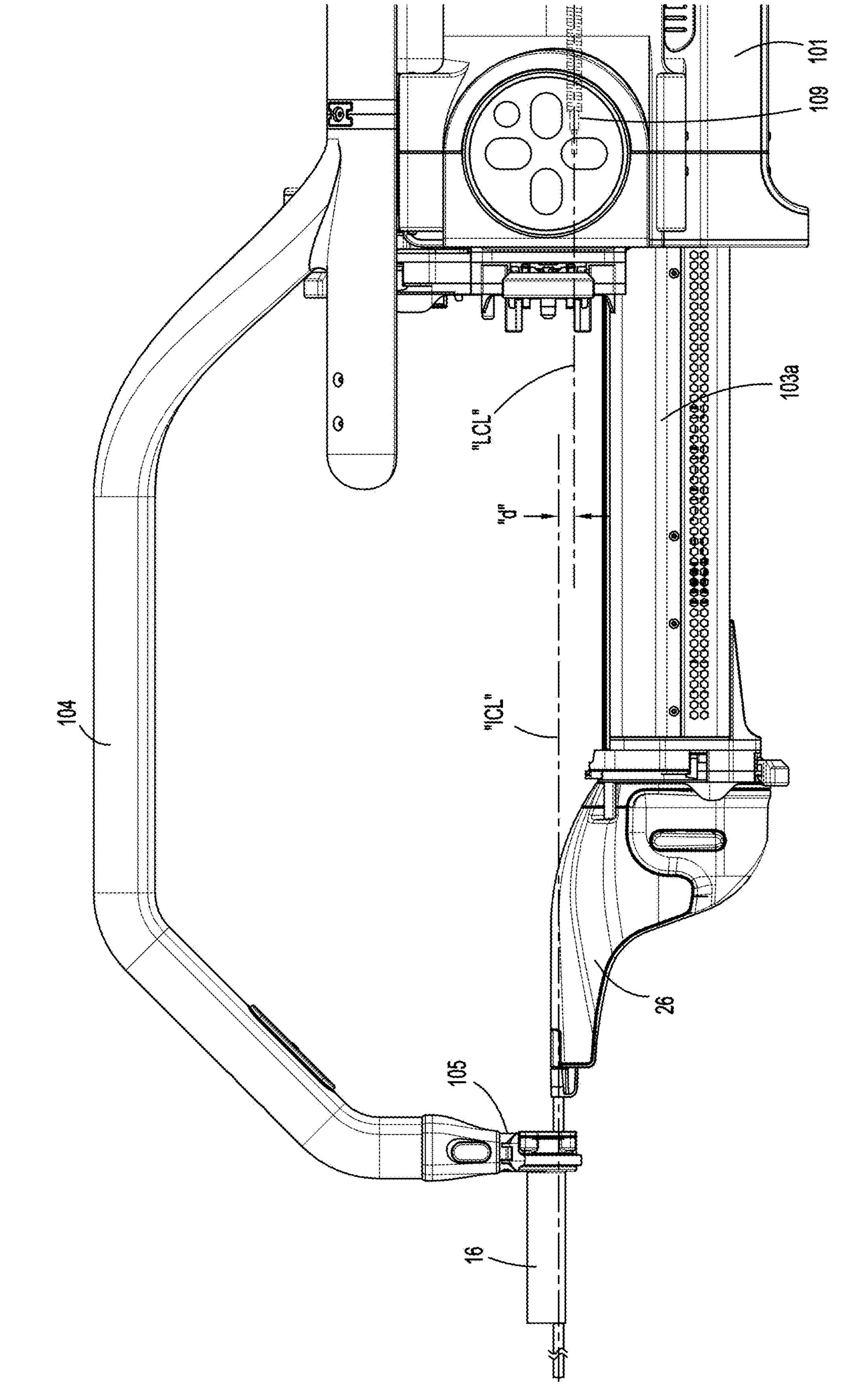
FIG. 31 is a side view of a distal portion of the control drive assembly of the robotic surgical system of FIG. 1 with one instrument drive unit of the control drive assembly supporting an instrument and shown in an advanced position relative to the control drive unit of the control drive assembly, the instrument shown positioned through the surgical portal assembly, the surgical portal assembly shown secured to the port latch assembly, wherein the other instrument drive units and the endoscope drive unit are shown in retracted positions relative to the control drive unit, the view further illustrating an offset relationship between an instrument centerline of the instrument and a leadscrew centerline of the leadscrew assembly of the control drive unit.

As seen in FIG. 31, each surgical instrument 26 defines an instrument centerline "ICL" and each respective leadscrew 109 that drives the instrument drive unit 103*a* supporting the respective surgical instrument 26 defines a leadscrew centerline "LCL." The leadscrew centerline "LCL" of the respective leadscrew 109 is positioned offset from the respective instrument centerline "ICL" by a distance "d" that is greater than zero (e.g., leadscrew centerline "LCL" and instrument center line "ICL" are parallel to one another).

The disclosed structure can include any suitable mechanical, electrical, and/or chemical components for operating the disclosed system or components thereof. For instance, such electrical components can include, for example, any suitable electrical and/or electromechanical, and/or electrochemical circuitry, which may include or be coupled to one or more printed circuit boards. As appreciated, the disclosed computing devices (and/or servers) can include, for example, a "controller," "processor," "digital processing device" and like terms, and which are used to indicate a microprocessor or central processing unit (CPU). The CPU is the electronic circuitry within a computer that carries out the instructions of a computer program by performing the basic arithmetic, logical, control and input/output (I/O) operations specified by the instructions, and by way of non-limiting examples, include server computers. In some aspects, the controller includes an operating system configured to perform executable instructions. The operating system is, for example, software, including programs and data, which manages hardware of the disclosed apparatus and provides services for execution of applications for use with the disclosed apparatus. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. In some aspects, the operating system is provided by cloud computing.

In some aspects, the term "controller" may be used to indicate a device that controls the transfer of data from a computer or computing device to a peripheral or separate device and vice versa, and/or a mechanical and/or electromechanical device (e.g., a lever, knob, etc.) that mechanically operates and/or actuates a peripheral or separate device.

In aspects, the controller includes a storage and/or memory device. The storage and/or memory device is one or more physical apparatus used to store data or programs on a temporary or permanent basis. In some aspects, the controller includes volatile memory and requires power to maintain stored information. In various aspects, the controller includes non-volatile memory and retains stored information when it is not powered. In some aspects, the non-volatile memory includes flash memory. In certain aspects, the non-volatile memory includes dynamic random-access memory (DRAM). In some aspects, the non-volatile memory includes ferroelectric random-access memory (FRAM). In various aspects, the non-volatile memory includes phase-change random access memory (PRAM). In certain aspects, the controller is a storage device including, by way of non-limiting examples, CD-ROMs, DVDs, flash memory devices, magnetic disk drives, magnetic tapes drives, optical disk drives, and cloud-computing-based storage. In various aspects, the storage and/or memory device is a combination of devices such as those disclosed herein.

In various aspects, the memory can be random access memory, read-only memory, magnetic disk memory, solid state memory, optical disc memory, and/or another type of memory. In various aspects, the memory can be separate from the controller and can communicate with the processor through communication buses of a circuit board and/or through communication cables such as serial ATA cables or other types of cables. The memory includes computer-readable instructions that are executable by the processor to operate the controller. In various aspects, the controller may include a wireless network interface to communicate with other computers or a server. In aspects, a storage device may be used for storing data. In various aspects, the processor may be, for example, without limitation, a digital signal processor, a microprocessor, an ASIC, a graphics processing unit ("GPU"), field-programmable gate array ("FPGA"), or a central processing unit ("CPU").

The memory stores suitable instructions and/or applications, to be executed by the processor, for receiving the sensed data (e.g., sensed data from camera), accessing storage device of the controller, generating a raw image based on the sensed data, comparing the raw image to a calibration data set, identifying an object based on the raw image compared to the calibration data set, transmitting object data to a post-processing unit, and displaying the object data to a graphic user interface. Although illustrated as part of the disclosed structure, it is also contemplated that a controller may be remote from the disclosed structure (e.g., on a remote server), and accessible by the disclosed structure via a wired or wireless connection. In aspects where the controller is remote, it is contemplated that the controller may be accessible by, and connected to, multiple structures and/or components of the disclosed system.

The term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on the disclosed controllers or on a user device, including for example, on a mobile device, an IoT device, or a server system.

In some aspects, the controller includes a display to send visual information to a user. In various aspects, the display is a cathode ray tube (CRT). In various aspects, the display is a liquid crystal display (LCD). In certain aspects, the display is a thin film transistor liquid crystal display (TFT-LCD). In aspects, the display is an organic light emitting diode (OLED) display. In certain aspects, on OLED display is a passive-matrix OLED (PMOLED) or active-matrix OLED (AMOLED) display. In aspects, the display is a plasma display. In certain aspects, the display is a video projector. In various aspects, the display is interactive (e.g., having a touch screen) that can detect user interactions/gestures/responses and the like. In some aspects, the display is a combination of devices such as those disclosed herein.

The controller may include or be coupled to a server and/or a network. As used herein, the term "server" includes "computer server," "central server," "main server," and like terms to indicate a computer or device on a network that manages the disclosed apparatus, components thereof, and/or resources thereof. As used herein, the term "network" can include any network technology including, for instance, a cellular data network, a wired network, a fiber-optic network, a satellite network, and/or an IEEE 802.11a/b/g/n/ac wireless network, among others.

In various aspects, the controller can be coupled to a mesh network. As used herein, a "mesh network" is a network topology in which each node relays data for the network. All mesh nodes cooperate in the distribution of data in the network. It can be applied to both wired and wireless networks. Wireless mesh networks can be considered a type of "Wireless ad hoc" network. Thus, wireless mesh networks are closely related to Mobile ad hoc networks (MANETs). Although MANETs are not restricted to a specific mesh network topology, Wireless ad hoc networks or MANETs can take any form of network topology. Mesh networks can relay messages using either a flooding technique or a routing technique. With routing, the message is propagated along a path by hopping from node to node until it reaches its destination. To ensure that all its paths are available, the network must allow for continuous connections and must reconfigure itself around broken paths, using self-healing algorithms such as Shortest Path Bridging. Self-healing allows a routing-based network to operate when a node breaks down or when a connection becomes unreliable. As a result, the network is typically quite reliable, as there is often more than one path between a source and a destination in the network. This concept can also apply to wired networks and to software interaction. A mesh network whose nodes are all connected to each other is a fully connected network.

In some aspects, the controller may include one or more modules. As used herein, the term "module" and like terms are used to indicate a self-contained hardware component of the central server, which in turn includes software modules. In software, a module is a part of a program. Programs are composed of one or more independently developed modules that are not combined until the program is linked. A single module can contain one or several routines, or sections of programs that perform a particular task.

As used herein, the controller includes software modules for managing various aspects and functions of the disclosed system or components thereof.

The disclosed structure may also utilize one or more controllers to receive various information and transform the received information to generate an output. The controller may include any type of computing device, computational circuit, or any type of processor or processing circuit capable of executing a series of instructions that are stored in memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, cause the one or more processors to perform one or more methods and/or algorithms.

The phrases "in an aspect," "in aspects," "in various aspects," "in some aspects," "in other aspects" or the like may each refer to one or more of the same or different aspects in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

Various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques).

Certain aspects of the present disclosure may include some, all, or none of the above advantages and/or one or more other advantages readily apparent to those skilled in the art from the drawings, descriptions, and claims included herein. Moreover, while specific advantages have been enumerated above, the various aspects of the present disclosure may include all, some, or none of the enumerated advantages and/or other advantages not specifically enumerated above.

The aspects disclosed herein are examples of the disclosure and may be embodied in various forms. For instance, although certain aspects herein are described as separate, each of the aspects herein may be combined with one or more of the other aspects herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

Any of the herein described methods, programs, algorithms, or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to all such states. Reference to a program may encompass the actual instructions and/or the intent of those instructions.

Securement of any of the components of the disclosed devices may be effectuated using known securement techniques such welding, crimping, gluing, fastening, etc.

Persons skilled in the art will understand that the structures and methods specifically described herein and shown in the accompanying figures are non-limiting exemplary aspects, and that the description, disclosure, and figures should be construed merely as exemplary of aspects. It is to be understood, therefore, that this disclosure is not limited to the precise aspects described, and that various other changes and modifications may be effectuated by one skilled in the art without departing from the scope or spirit of the disclosure. Additionally, the elements and features shown or described in connection with certain aspects may be combined with the elements and features of certain other aspects without departing from the scope of this disclosure, and that such modifications and variations are also included within the scope of this disclosure. Accordingly, the subject matter of this disclosure is not limited by what has been particularly shown and described.

What is claimed is:

1. A robotic surgical system, comprising:

an instrument cart having a setup arm assembly; and a control drive assembly coupled to the setup arm assembly, the control drive assembly including:

a chassis assembly, wherein the chassis assembly includes a spinebox assembly;

a first drive unit and a second drive unit mounted to the chassis assembly, each drive unit of the first and second drive units positioned to translate relative to the chassis assembly between a retracted position and an advanced position, the first drive unit configured to couple to a first surgical instrument, the second drive unit configured to couple to a second surgical instrument, wherein the first and second drive units are movably mounted to the spinebox assembly; and a leadscrew assembly supported by the spinebox assembly of the chassis assembly, the leadscrew assembly including a first leadscrew operably associated with the first drive unit and a second leadscrew operably associated with the second drive unit, the first leadscrew being rotatable to cause the first drive unit to translate relative to the chassis assembly, the second leadscrew being rotatable to cause the second drive unit to translate relative to the chassis assembly, wherein:

the first leadscrew supports a first slide plate assembly that engages with the first drive unit and the second leadscrew supports a second slide plate assembly that engages with the second drive unit, the first and second slide plate assemblies are movable through the spinebox assembly to move the first and second drive units relative to the spinebox assembly, and the first slide plate assembly includes drive pins extending therefrom, the drive pins being positionable within the first drive unit to couple the first slide plate assembly to the first drive unit.

2. The robotic surgical system of claim 1, wherein the first slide plate is threadedly coupled to the first leadscrew, the first slide plate positioned to translate along the first leadscrew as the first leadscrew is rotated relative to the first slide plate.

3. The robotic surgical system of claim 1, wherein the first drive unit includes a first motor assembly supporting a first plurality of motors configured to operate the first surgical instrument, and wherein the second drive unit includes a second motor assembly supporting a second plurality of motors configured to operate the second surgical instrument.

4. The robotic surgical system of claim 1, wherein the leadscrew assembly further includes a drive assembly supported on the chassis assembly, the drive assembly including at least one leadscrew drivetrain motor that mounts to the chassis assembly, the at least one leadscrew drive train motor operatively coupled to at least one drive gear, the at least one drive gear being rotatable by the at least one leadscrew drivetrain motor to rotate at least one of the first or second leadscrews.

5. A control drive assembly for a robotic surgical system, the control drive assembly comprising:

a chassis assembly supporting a leadscrew assembly, the leadscrew assembly including a plurality of leadscrews;

an endoscope drive unit coupled to an endoscope;

a first instrument drive unit coupled to a first surgical instrument;

a second instrument drive unit coupled to a second surgical instrument; and a third instrument drive unit coupled to a third surgical instrument, wherein the endoscope drive unit and each instrument drive unit are mounted to the chassis assembly, wherein each drive unit is movable relative to the other drive units to move the endoscope, the first surgical instrument, the second surgical instrument, or the third surgical instrument between extended and retracted positions relative to the chassis assembly in response to rotation of at least one leadscrew of the plurality of leadscrews; and a manual release assembly including at least one release knob operatively coupled to the leadscrew assembly, the at least one release knob being rotatable to manually rotate at least one of the plurality of leadscrews.

6. A robotic surgical system, comprising:

a setup arm assembly; and a control drive assembly pivotably coupled to the setup arm assembly, the control drive assembly including:

an endoscope;

a surgical instrument; and a control drive unit, the control drive unit including:

a chassis assembly;

an endoscope drive unit mounted to the chassis assembly and removably supporting the endoscope;

an instrument drive unit mounted to the chassis assembly and removably supporting the surgical instrument;

a first leadscrew operably associated with the endoscope drive unit, the first leadscrew being rotatable to cause the endoscope drive unit to translate relative to the chassis assembly; and a second leadscrew operably associated with the instrument drive unit, the second leadscrew being rotatable to cause the instrument drive unit to translate relative to the endoscope drive unit.

7. The robotic surgical system of claim 6, wherein the surgical instrument defines an instrument centerline and the second leadscrew defines a leadscrew centerline, the instrument centerline and the leadscrew centerline being offset.

8. The robotic surgical system of claim 6, wherein the control drive unit includes a support bar assembly, wherein movement of the support bar causes the control drive unit to pivot relative to the setup arm assembly.

9. The robotic surgical system of claim 8, wherein the support bar assembly includes a first portion and a second portion that are selectively attachable to one another about the chassis assembly by a joint.

10. The robotic surgical system of claim 9, wherein the first portion of the support bar assembly is arched distally to a port latch assembly, the port latch assembly including a fixed clamp arm and a pivotable clamp arm, the pivotable clamp arm is positioned to pivot relative to the fixed clamp arm to secure a surgical portal assembly to the support bar assembly.

11. The robotic surgical system of claim 10, wherein the surgical portal assembly defines a first lumen therethrough configured to receive the endoscope and a second lumen therethrough configured to receive the surgical instrument therethrough.

12. The robotic surgical system of claim 11, wherein the surgical portal assembly has a proximal housing that defines a first annular channel configured to receive the fixed clamp arm therein and a second annular channel configured to receive the pivotable clamp arm therein.

13. The robotic surgical system of claim 11, wherein at least one of the first or second lumens includes a lofted distal portion to enable greater shaft deflections of the endoscope or the surgical instrument at the distal end portion of the surgical portal assembly in comparison to a proximal portion of the surgical portal assembly.

14. The robotic surgical system of claim 6, wherein the setup arm assembly includes a control pad that is actuatable to cause at least one of the endoscope drive unit or the instrument drive unit to move relative to the chassis assembly, and wherein the setup arm assembly includes at least one brake assembly configured to limit movement of the endoscope drive unit and the instrument drive unit relative to the chassis assembly.

15. The robotic surgical system of claim 6, wherein the instrument drive unit includes a first sterile adapter assembly secured thereto and the endoscope drive unit includes a second sterile adapter assembly secured thereto, each of the first and second sterile adapter assemblies supports drive dogs therein, and wherein at least one of the endoscope drive unit or the instrument drive unit includes a drive dog alignment tool that pre-aligns the drive dogs of the respective first or second sterile adapter assemblies for facilitating attachment of the respective endoscope or surgical instrument to the respective first or second sterile adapter assemblies.

* * * * *